US007850303B2

(12) United States Patent
Reichow et al.

(10) Patent No.: US 7,850,303 B2
(45) Date of Patent: Dec. 14, 2010

(54) OPTICALLY DECENTERED FACE SHIELD

(75) Inventors: Alan W. Reichow, Forest Grove, OR (US); Karl Citek, Forest Grove, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 12/117,492

(22) Filed: May 8, 2008

(65) Prior Publication Data

US 2008/0212019 A1 Sep. 4, 2008

Related U.S. Application Data

(63) Continuation of application No. 10/883,399, filed on Jun. 30, 2004, now Pat. No. 7,389,543.

(51) Int. Cl.
*G02C 7/02* (2006.01)
*G02C 5/00* (2006.01)
*A41D 13/00* (2006.01)
*A63B 71/10* (2006.01)

(52) U.S. Cl. ...................... 351/159; 351/41; 2/9; 2/425

(58) Field of Classification Search .................. 351/41, 351/159; 2/9–10, 15, 425, 426–434
See application file for complete search history.

(56) References Cited

U.S. PATENT DOCUMENTS 5,689,323 A * 11/1997 Houston et al. ............... 351/41
6,010,217 A * 1/2000 Houston et al. ............. 351/159
6,715,150 B1 * 4/2004 Potin .............................. 2/15

* cited by examiner

*Primary Examiner*—Joseph Martinez
*Assistant Examiner*—James R Greece
(74) *Attorney, Agent, or Firm*—Shook Hardy & Bacon LLP

(57) ABSTRACT

A face protector includes a one piece shield in which an optical center is displaced away from the normal straight ahead line of sight toward an activity specific line of sight to minimize image shift that occurs when a direction of gaze passes across the edge of the shield. An apex of the shield is formed at a forwardmost point of the shield, or a virtual extension of the shield, when the shield is in an as worn position on a wearer. In particular examples, an optical axis extends through the optical center, at a non-zero angle to the normal straight ahead line of sight and substantially parallel to the activity specific line of sight, with the optical center being placed away from the apex. In particular examples, the optical axis is closer to (or coincident with) an activity specific line of sight of one of the right or left eye. The face protector is particularly useful in activities such as sports, for example hockey, football, or baseball which involve activity specific lines of sight. In one disclosed embodiment, the optical center is positioned at or below a bottom edge of the shield so that a hockey player can view an object on the ice below the lower edge of the shield with reduced image shift.

31 Claims, 13 Drawing Sheets

OPTICALLY DECENTERED FACE SHIELD

CROSS-REFERENCE TO RELATED APPLICATIONS

This application is a continuation of U.S. application Ser. No. 10/883,399 filed Jun. 30, 2004, now pending, entitled "Optically Decentered Face Shield."

STATEMENT REGARDING FEDERALLY SPONSORED RESEARCH OR DEVELOPMENT

Not applicable.

TECHNICAL FIELD

This disclosure concerns protective shields with improved optics that optimize visual performance.

BACKGROUND OF THE INVENTION

There is an increasing demand for eye and face protection for people who participate in sports and other activities that can potentially damage the eyes or other facial structures. Eye injuries (sometimes leading to loss of vision) can occur in sports such as hockey and football in which objects (such as sticks, pucks, or another player's elbows or fingers) can strike a participant's eye or face with destructive velocity and force. Protective shields are also used for a variety of non-sports related tasks, such as mowing lawns or hammering nails, to help prevent inadvertent projectiles from injuring the eye or face. An increased awareness of the potentially infectious nature of body fluids has also prompted many health care professionals to wear protective eyewear or face shields when treating patients, to avoid accidental infections from blood, saliva or other fluids splattered into the eye or on other mucus membranes.

One drawback to the use of protective face shields is that shields can distort the wearer's vision. Early face shields were merely a flat sheet of plastic bent into an arcuate shape to conform to the facial contour. However such a shield causes significant optical distortion that can be distracting to the wearer, and cause serious performance problem in persons who require precise visual input, such as athletes, pilots and surgeons.

The prior art is replete with examples of efforts to overcome optical distortion in protective eyewear. Rayton's U.S. Pat. No. 1,741,536 (issued in 1929 to Bausch & Lomb) discloses a protective goggle in which the front and back surfaces of the lenses were defined by two spheres having offset centers. An optical centerline (optical axis) through the centers of the spheres is spaced from, and oriented parallel to, a direct straight ahead line of sight. This optical configuration provides a tapered lens, in which the lens thickness gradually decreases symmetrically from the optical center toward the edges. Maintaining the line of sight parallel to the optical axis helps neutralize the distortion that would otherwise be caused by wrapping the lenses laterally with respect to the eye.

The problem of distortion in a face shield was also addressed in U.S. Pat. No. 4,271,538 (the Montesi patent), which disclosed an optically corrected shield having spherical inner and outer surfaces that defined an optical center C over the bridge of the nose. The thickness of the shield tapers in all directions away from the optical center C, which is the thickest portion of shield. As shown in Table I of that patent, the lens can have a small amount of minus power (±0.03 diopters), and minimizes viewing distortion. Since the optical centerline of this spherical lens is through the optical center C, the optical centerline is spaced from and parallel to the normal (straight ahead) line of sight, as in the Rayton patent.

In the 1980s, the Foster Grant Company sold dual lens Eyeguard protective eyewear, having a spherical lens in front of each eye with both wrap and pantoscopic tilt. As in the Rayton patent, the optical axis of each lens is spaced from and maintained parallel to the straight-ahead/normal line of sight. The optical centerline is horizontally and vertically offset from, as well as parallel to, the normal line of sight. The horizontal and parallel offset of these lines helps neutralize the distortion caused by lateral wrap of the lens, while the vertical and parallel offset helps neutralize the distortion caused by pantoscopic tilt.

A similar "optically corrected" face shield lens is shown in U.S. Pat. No. 6,010,217 which issued to Oakley, Inc. This patent discloses a face shield having a spherical lens in which the optical centerline is horizontally and vertically spaced from and substantially parallel to the normal line of sight when the shield is worn. The optical axis of these shields passes through the apex of the shield, which is the forward-most point of the shield in the as worn condition. Hence the optical center of the shield is at the apex. This is the same approach that was disclosed by Montesi as early as 1981.

U.S. Pat. Nos. 5,815,848 and 6,038,705 also issued to Oakley, and disclose a low power "optically correct" face shield having a thickest portion at the center of the lens, from which the lens tapers in all directions, as in Montesi's U.S. Pat. No. 4,271,538. This design was also used in visors of military helmets during the 1980s.

A variety of eyewear designs have also been proposed to address the visual demands of particular sports. U.S. Pat. No. 5,614,964 discloses dual lens eyewear, especially adapted for cycling and alpine skiing, in which each lens has an exterior lens surface with a single center of curvature. The inner radius of curvature of each of the right and left lenses is greater than the outer radius of curvature. The centers of curvature of the inner spheres are also offset horizontally and vertically.

U.S. Pat. No. 5,457,502 discloses eyeglasses particularly suited for a person who is bending forward and looking ahead, such as a bicyclist. An upper spherical portion of the lens has a different radius of curvature than the lower spherical portion of the lens, to enhance visual clarity when the cyclist is leaning forward and looking up.

U.S. Pat. No. 5,555,038 also shows spherical lenses for use in eyewear. The centers of curvature of the right and left lenses are horizontally separated by a distance of 0.1 to about 4.0 em. This geometry is said to help ensure that the lenses fit closely over each eye without distorting or blocking vision of the wearer in the central portion of the lens.

SUMMARY OF THE INVENTION

If a wearer shifts a direction of gaze such that the line of sight is significantly not parallel to the optical axis of a lens, but still through the shield, the shield will produce substantial distortion, such that the image is perceived to be in a different location than the actual object. This shift is even more pronounced when a wearer shifts a direction of gaze between the shield and the surroundings, producing a jump in the visual image caused by the change in refraction as the line of gaze passes across the edge of the shield.

These problems are addressed in the present disclosure by a protective shield to be mounted in an as worn orientation in front of the face of a wearer for a sight specific activity that involves an activity specific line of sight (ASLS) that is different than a normal straight ahead line of sight (NLOS). The shield extends across the eyes and nose of the wearer, and has an optical axis extending through an optical center that is substantially parallel to but shifted in the direction of the ASLS to minimize image shift as a line of gaze moves toward the ASLS. For example, if the ASLS is near the bottom edge of the shield, the optical center is shifted toward or below the bottom edge of the shield, such that the optical axis is spaced from and substantially parallel to the activity specific line of sight. This arrangement minimizes image shift when the wearer's gaze is in that lower zone of the shield and if the wearer's gaze moves from the lower shield to below the shield.

In some particularly disclosed embodiments, the shield includes an arcuate face protector lens having a sight line across the shield through which both of a wearer's normal straight ahead lines of sight extend when the face protector is worn. The optical axis of the shield extends through the optical center below the sight line of the shield, for example below the apex of the shield, which is the forwardmost point of the lens in the as worn orientation. In a disclosed embodiment, the optical center is below the bottom edge of the lens, for example at least 5 mm or 10 mm below the lower edge of the lens. The bottom edge of the lens is also the thickest edge, from which the thickness of the lens tapers. In particular embodiments the lens is a spherical lens having a power of −0.12 to +0.12 diopters, for example a zero power lens, or a toroidal lens having different radii of curvature in the horizontal and vertical planes. In other embodiments, the lens tapers symmetrically with respect to an optical center point that is below the lower edge of the lens, for example below the midpoint of the lower edge. Hence a thickness of the lens tapers from the lower thicker edge to the top thinner edge, and the lateral edges of the lens similarly taper from the bottom toward the top of the lens. In particular examples, the protective shield has an optical axis that extends through its optical center (where the optical center can be on or off the shield), and the optical axis is substantially parallel to and horizontally and vertically displaced from the ASLS of a right eye and a left eye. In other embodiments, the optical axis is substantially equidistant between the ASLS of the right eye and the left eye, and in a plane that includes both the ASLS of the right eye and the ASLS of the left eye. In yet other embodiments, the optical axis is substantially closer to or coincident with the ASLS of one eye compared to that of the fellow eye. In certain examples in which the optical axis is closer to one eye than the other, the optical axis is substantially parallel to and displaced laterally in the direction in which a direction of gaze is directed. For example, if gaze is directed down and to the right, the optical axis is substantially parallel to the ASLS of each eye, but closer to the ASLS of the right eye than the left eye. For example, depending on the angle of the ASLS to the NLOS, the optical axis may be between the ASLS of the right and left eye, coincident with the ASLS of the right eye, or not between the ASLS of the right and left eye but still closer to the ASLS of the right eye than the ASLS of the left eye. If gaze is directed up and to the left, the optical axis is substantially parallel to the ASLS of each eye, but closer to the ASLS of the left eye then the right eye. For example, the optical axis may be between the ASLS of the right and left eye, coincident with the ASLS of the left eye, or not between the ASLS of the right and left eye but still closer to the ASLS of the left eye than the ASLS of the right eye.

The shields disclosed herein generally are relatively low base lenses that may be spherical or non-spherical (for example toroidal). A spherical lens has a single radius of curvature that defines each surface, while a toroidal lens may have different radii of curvature in perpendicular meridians. For example, a toroidal lens surface may have a first radius of curvature in a horizontal meridian and a second (different) radius of curvature in a vertical meridian. In particular examples, the shields disclosed herein have a base curve of 2-7 diopters, for example 4-6 diopters. In certain toroidal examples, the shield may have different horizontal and vertical curvatures within these ranges, or significant curvature in only one meridian (such as a shield that curves horizontally across the face but not vertically). In such an example, the base curve in one meridian (such as the vertical meridian) may be 0-4, for example O.

Methods are also disclosed for protecting the face of a subject by mounting the lens in front of the face, for example by attaching it to a helmet worn by the subject. The lens is mounted in front of the face, with the optical center at or beyond the edge of the lens across which the line of sight moves to the activity specific line of sight. For example, a hockey shield lens is mounted with an optical center below the lower edge of the shield lens, so that a hockey player's gaze can shift between the lens and an ice surface (for example to view a hockey puck) while minimizing image shift.

Methods are also disclosed for reducing image distortion of the shield by cutting away peripheral portions of a molded lens. Elimination of peripheral molded material can diminish optical distortion or image jump that would otherwise be encountered if the original molded material were left in place on the shield. It is particularly helpful to cut away portions of the shield along edges across which the wearer's gaze passes when moving from a normal line of sight to an activity specific line of sight. This method is of general use in any shield in which reduction of peripheral distortion is desired, and it can be used to make the shields disclosed herein that incorporate corrected optics, or other shields that do not incorporate the corrected optics disclosed herein in which the optical center is aligned with the activity specific line of sight.

The foregoing and other features and advantages of the invention will become more apparent from the following detailed description of several embodiments which proceeds with reference to the accompanying figures.

BRIEF DESCRIPTION OF THE SEVERAL VIEWS OF THE DRAWINGS

FIG. 6 illustrates the horizontal and vertical position of the optical center in a shield designed for an activity specific line of sight. The optical center is vertically displaced in a vertical midline of the shield. FIG. 6B illustrates that the optical axis is parallel to and spaced from the ASLS, and equidistant between the ASLS of the right and left eyes.

DETAILED DESCRIPTION OF THE INVENTION

Abbreviations

Figure 1:
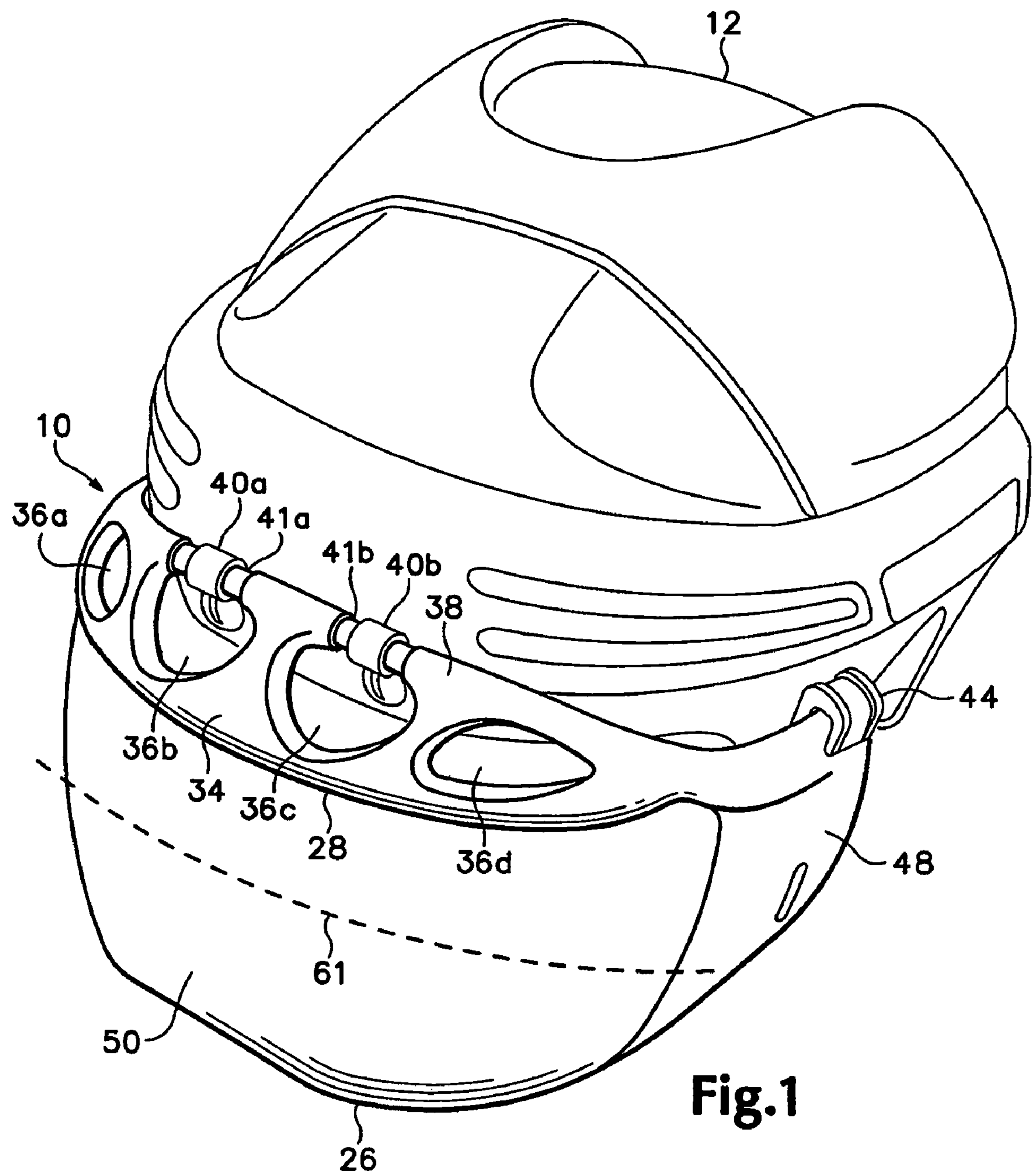
FIG. 1 is a perspective view of the protective shield mounted to a helmet.

APX: Apex
ASLS: Activity Specific Line of Sight
$C_1$: Center(s) of curvature of front shield surface
$C_2$: Center(s) of curvature of rear shield surface
PF: Frontal Plane
GC: Geometric Center
L: Left, usually with reference to the left eye
MP: Median Plane
NLOS: Normal Line of Sight
NLOS R: Normal Line of Sight of the right eye
NLOS L: Normal Line of Sight of the left eye
OA: Optical Axis
OAh: Optical Axis horizontal component
OAv: Optical Axis vertical component
OC: Optical Center
R: Right, usually with reference to the right eye
Rfh: Front surface Radius of curvature horizontal meridian
Rfv: Front surface Radius of curvature vertical meridian
Rrh: Rear surface Radius of curvature horizontal meridian
Rrv: Rear surface Radius of curvature vertical meridian.

Terms

To facilitate an understanding of the terms used in the specification and claims, some of those terms are discussed in this section.

The "normal line of sight," which is also referred to as the NLOS, is a fixed line that projects forward from each eye when the eyes are fixed on a distant point. The NLOS can refer to the line of sight of a single eye or both eyes (because the direction of gaze is normally maintained in the same direction by brainstem reflexes to avoid diplopia). The NLOS of the two eyes extend in a generally horizontal plane through the eyes when the head is in an upright position with the eyes staring into the distance. When the head is not in the upright position the NLOS extends in a transverse (anterior-posterior) plane of the head through the eyes. A particularly convenient way to determine a NLOS is to place eyewear or a shield on a conventional headform (such as an Alderson or Canadian head form) which has been designed based on a statistical norm for a population. The position of the NLOS (or the plane that contains the NLOS of the two eyes) can be determined by reference to this headform, which can readily establish a normative position for a population.

An "activity specific line of sight" is abbreviated ASLS, and is a determinable direction of gaze for performing a particular activity. Since the direction of gaze is yoked for the two eyes, the ASLS of each eye is substantially parallel, or slightly convergent, in a common plane (referred to herein as the activity specific line of sight plane ASLS P). The ASLS is generally determinable for a population performing a particular activity, such as a particular recreational or occupational activity.

Particular examples of an ASLS include a downward gaze for a hockey player whose sight is fixed on an ice puck on a rink; a lateral gaze for a baseball player who is standing in a batting stance looking toward a pitcher; and an upward gaze for a football player who is playing at a position that requires looking up to catch a football (such as a receiver looking up at an approaching passed ball). All of these activities involve activity specific lines of sight that require optimal visual performance at a time when a direction of gaze is averted from a straight ahead direction for which most protective shields (such as hockey, batting or football helmets) have optimized optical performance.

The terms "horizontal plane" and "vertical plane" refer to horizontal and vertical planes when the head is in the upright position.

A median plane (MP) is a unique plane that passes longitudinally through the middle of the body from front to back and divides the head into right and left halves. A frontal plane (FP) is anyone of a series of planes passing through the body from side-to-side, at right angles to the median plane, or a plane that is parallel to such a plane. Some frontal planes divide the body into front and back parts. Any frontal plane and the median plane are perpendicular to one another.

An "apex" of a shield or lens refers to a forwardmost point of the shield or lens in the as worn condition with the head in the neutral upright and straight ahead position. An apex can be on the shield or lens itself, or on a virtual extension thereof.

A "virtual extension" refers to a position that would be on the shield or lens if the optical surfaces extended beyond the borders of the shield or lens.

The "geometric center" of a lens is the center of a rectangle that circumscribes each frame aperture from a frontal perspective. The location of the geometric center can easily be located at the intersection of diagonals of each rectangle, or the intersection of perpendicular bisectors of the horizontal (A) and vertical (B) dimensions. The distance between the centers (DBC) is the distance between the geometric centers of the two apertures of the frame. The concept of a geometric center can also be applied to a lens blank. For example, a lens blank having a circular outline has a geometric center at the axis of symmetry of the lens blank that extends perpendicularly through the lens blank at its center.

"Substantially parallel" means within 15 degrees of parallel, for example within 5 or 10 degrees of parallel, or even within 2 degrees of parallel.

In certain examples, the optical axis is said to be parallel or substantially parallel to the ASLS of each eye, and closer to the ASLS of either the right eye or the left eye. The optical axis is considered closer to the ASLS of one of the eyes if the minimum measured distance in millimeters between the optical axis and the parallel ASLS of the one eye is less than the minimum measured distance in millimeters between the optical axis and the parallel ASLS of the other eye. The measurement of the minimum distance between two parallel lines will be evident to one of skill in the art as the length between the two parallel lines of a line that horizontally intersects the two parallel lines.

Embodiment of FIGS. 1-5

Figure 2:
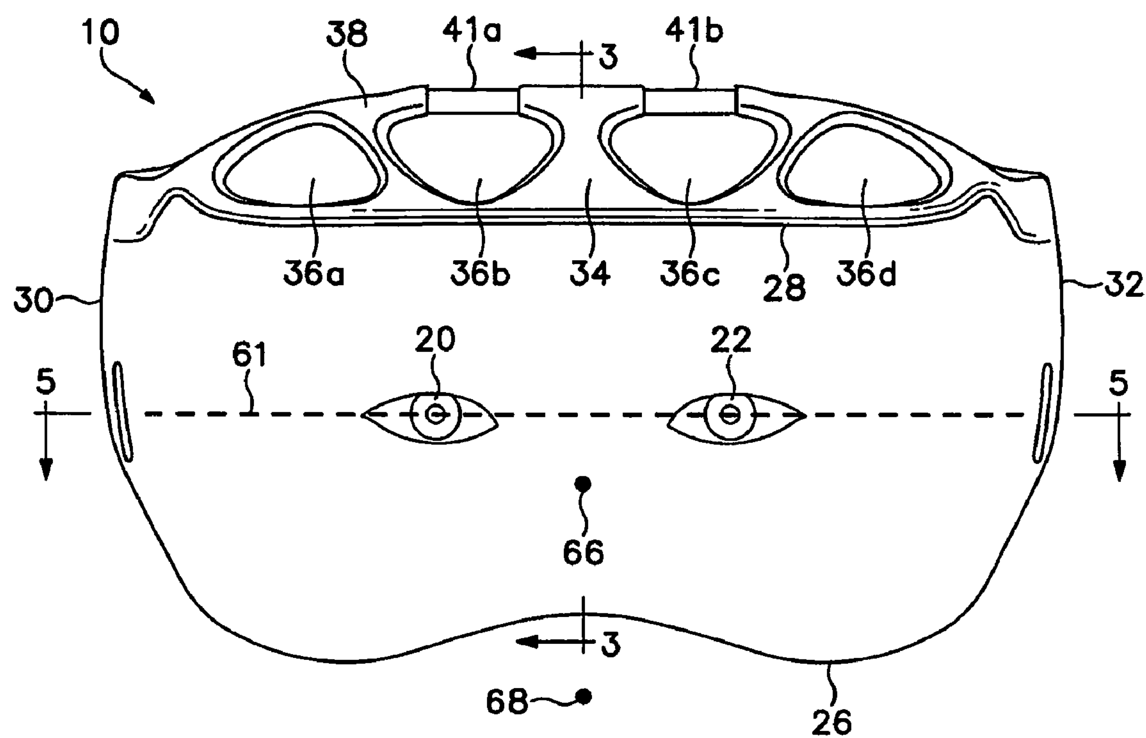
FIG. 2 is an isolated front elevational view of the shield shown in FIG. 1, with the position of the normal straight ahead lines of sight (and the sight line that they intersect) illustrated schematically.
Figure 3:
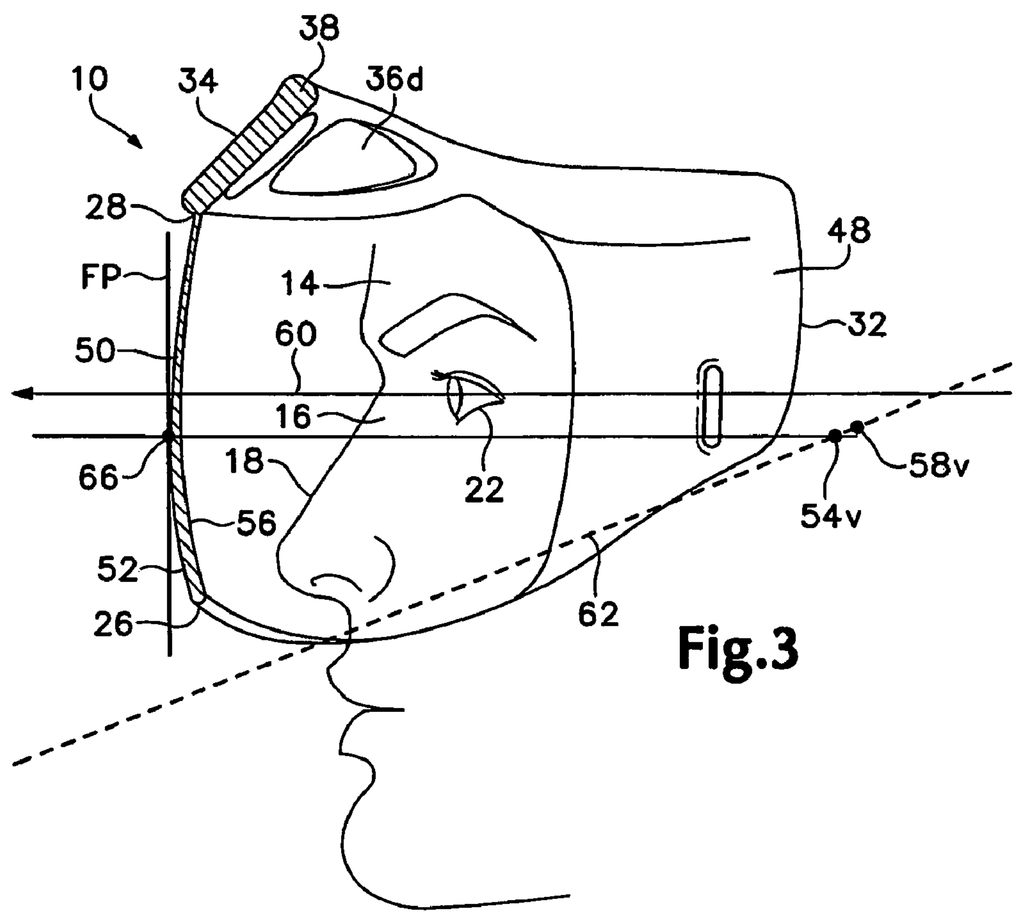
FIG. 3 is a vertical cross-sectional view of the shield along lines 3-3 of FIG. 2, with the shield shown mounted to a helmet on the head of a wearer, and schematically illustrating the optical axis and straight ahead line of sight; as well as the apex line that extends through the apex (forwardmost point) of the shield and the front center of curvature of the vertical centers of curvature.

One example of an optically improved one-piece face shield 10 is shown in FIGS. 1-5. In this embodiment, shield 10 is mounted to a helmet 12 that is worn by a subject. When helmet 12 is in place on the head 14 (FIG. 3) of the subject, shield 10 is held in front of the face 16 so that the shield protects nose 18 (FIG. 3) and eyes 20, 22 (FIGS. 2 and 3). In the illustrated embodiment, the shield extends through an arc of more than 180 degrees across the front of the face and over the temples, and from the top of the helmet, down over the forehead to between the nose and upper lip. The shield therefore protects the forehead, temples, eyes, nose and cheek bones (zygomatic arch).

Shield 10 has a lower edge 26, an upper edge 28, and side edges 30, 32. An inclined frame member 34 extends along top edge 28 and contains a plurality of perforations 36*a*, 36*b*, 36*c*, and 36*d* that form vents for shield 10 between top edge 28 and a substantially cylindrical beaded edge 38 of frame member 34. Frame member 34 can either be unitary with or separate from shield 10. Two cylindrical plastic hinge members 40*a* and 40*b* extend from the front of helmet 12, and encircle reduced diameter portions 41*a* and 41*b* of beaded edge 38 to pivotally mount shield 10 to helmet 12 in a manner that allows shield 12 to rotate between a fixed, protective position shown in FIGS. 1-5, to an open position (not shown) in which shield 10 does not cover the face. A guide stop flange 44 is mounted at each temple of helmet 12 such that a top edge of side supports 46, 48 (FIGS. 1 and 5) of frame member 34 engages stop flange 44 when shield 10 is in the desired closed (face-protecting) orientation.

Figure 5:
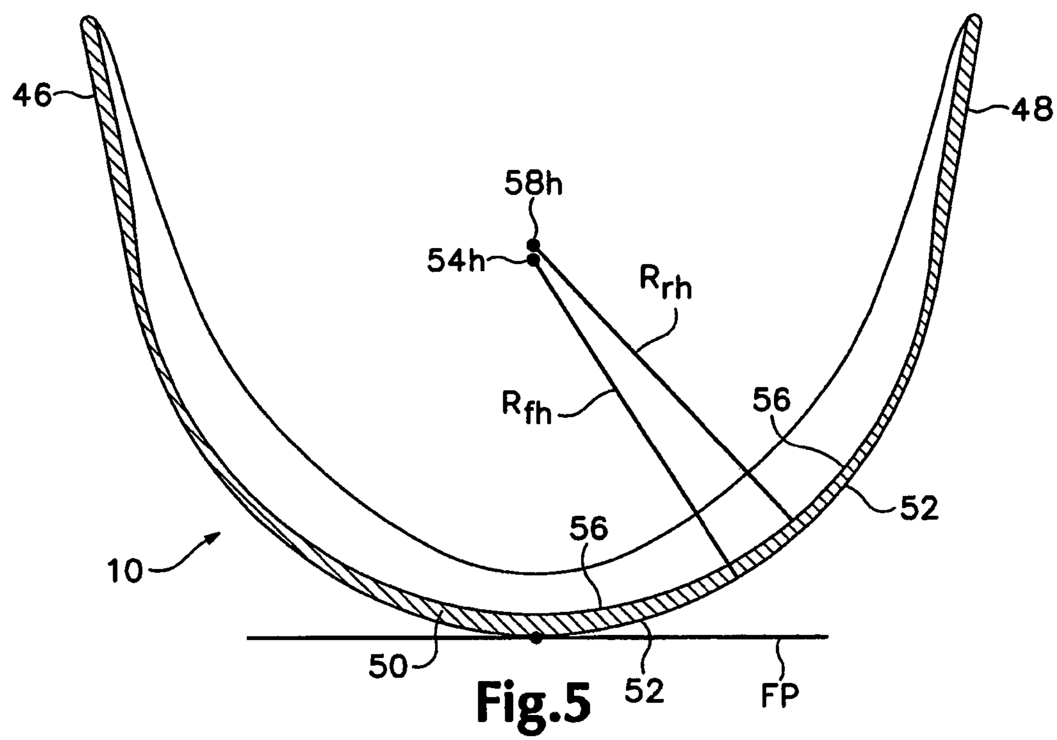
FIG. 5 is a horizontal cross-sectional view taken along line 5-5 in FIG. 2, showing the front and back radii of curvature in the horizontal plane.

The front portion of shield 10 forms a clear one-piece lens 50 that extends below frame member 34 across the eyes and nose, between side supports 46, 48. The junction between lens 50 and side supports 46, 48 is illustrated in FIG. 5, at which point the thickness of shield 10 substantially thickens.

Figure 4:
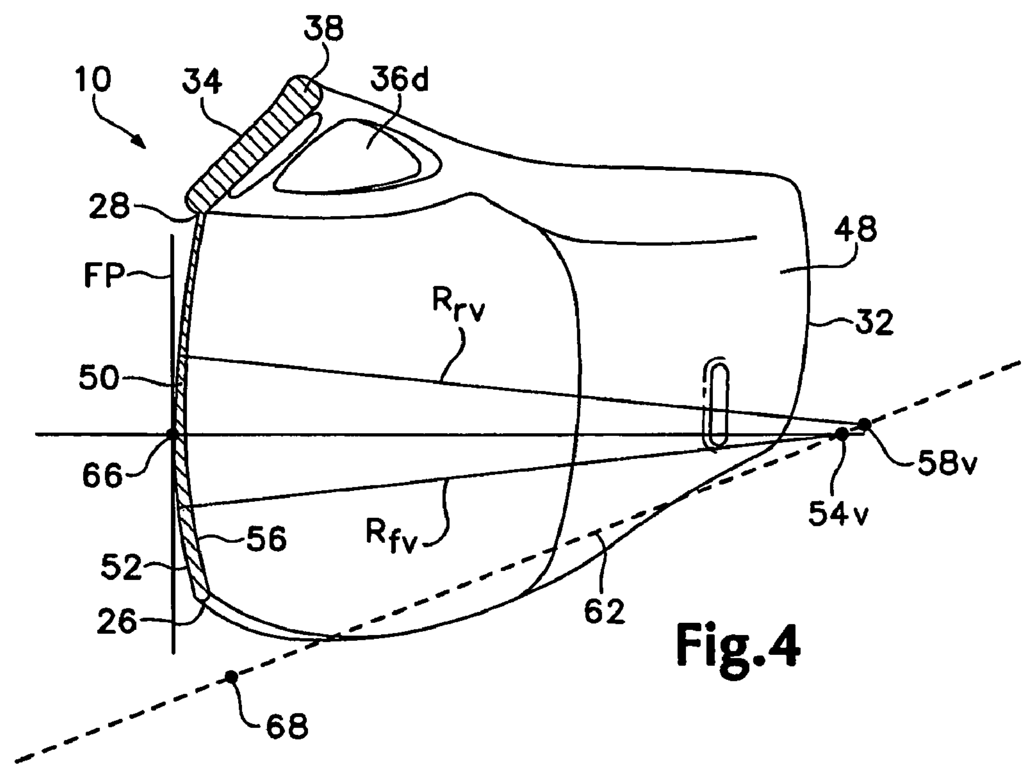
FIG. 4 is an isolated view of the shield shown in FIG. 3, showing the front and back radii of the shield in the vertical plane.

Lens 50 can have a variety of optical configurations, such as spherical, cylindrical, toroidal, or aspheric, and is preferably made of plastic of sufficient thickness to provide adequate protection of the face from impact. The disclosed embodiment of lens 50 is of non-uniform thickness, and it tapers across its height and width from a center thickness CT point that may be on or off the lens. In the illustrated embodiment, lens 50 excludes the frame portion of shield 10 (such as frame member 34 and side supports 46, 48) and lens 50 is itself toroidal as shown in FIGS. 3-5.

In a preferred embodiment, lens 50 has a front surface 52 that conforms to the surface of a torus having front centers of curvature 54*h* and 54*v* (FIGS. 4 and 5) with respective front radii of curvature Rfh (in the horizontal plane) and Rfv (in the vertical plane), and has a rear surface that conforms to the surface of a torus having rear centers of curvature 58*h* and 58*v* (FIGS. 4 and 5) with rear radii of curvature Rrh (in the horizontal) and Rrv (in the vertical). In the spherical embodiment of the lens, Rfh and Rfv are equal, centers of curvature 54*h* and 54*v* are coincident, Rrh and Rrv are equal, and centers of curvature 58*h* and 58*v* are coincident. In a plane cylinder embodiment of the lens, the corresponding front and rear radii of curvature in one meridian are infinite in length.

If the corresponding front and rear centers of curvature of a curved lens are coincident, this relationship of the front and rear surfaces would produce a lens having minus power. In examples in which lens 50 has zero power, the desired radii of curvature can be determined using the lens power equation. Similarly, a lens having a small amount of lens power can be provided. In the particularly disclosed embodiments, the lens is a non-corrective lens having a dioptric power (plus or minus power) of less then 0.25 diopters, and in particular less then 0.12 diopters. In especially preferred examples, the power of the lens is less than 0.06 diopters.

As best shown in FIG. 3, shield 10 is mounted in front of the face of a wearer such that it intersects a NLOS 60 of the wearer. The NLOS 60 for each eye intersects lens 50 along a transverse sight line 61 (FIG. 1) of lens 50, that extends from side to side across the lens in a transverse anatomical plane that would intersect the head of the wearer. Sight line 61 therefore lies in a NLOS plane that includes the normal lines of sight of both eyes 20, 22. Each NLOS 60 extends through the center of rotation of the eye and the pupil, along a sight line of a person looking straight ahead into the distance.

An optical axis 62 (FIG. 3) of the lens extends through the centers of curvature of the front and rear surfaces 52, 56 of lens 50. In a sphere or plane cylinder, the optical axis extends through the two centers of curvature of the front and rear surface meridians that are curved. In a spherocylinder, the optical axis extends through the center of curvature of the spherical surface and the two centers of curvature of the principal meridians of the cylindrical surface. In a toroid, the optical axis extends through the four centers of curvature of the principal meridians of the front and rear surfaces. It is well understood by those skilled in the art that any of these surfaces in these embodiments also may be generated with aspheric curvatures.

The parameters of lens 50 that contribute to its optical performance include surface curvatures, separations of centers of curvature, center thickness, and material index of refraction. Practical considerations in the lens design include such factors as relative impact resistance, minimum thickness requirements, lens position and orientation with respect to the wearer, field of view requirements for the wearer, facial morphology of the wearer, and lens carrier system (e.g., helmet, goggle, spectacle). For example, a non-corrective plastic lens designed for use as an occupational protective face shield conforming to ANSI standards must have a minimum thickness at any lens location of 1 mm. In another example, a non-corrective lens designed to be worn as a hockey face shield mounted to a helmet will have a horizontal curvature of about 5-6 diopters and a vertical curvature of about 2-3 diopters. In yet another example, a lens manufactured from CR-39 or acrylic, both with refractive indices of about 1.5, would require different surface curvatures and center thickness compared to a lens manufactured from polycarbonate, with refractive index of about 1.59, to produce a final lens with equivalent total power. Table 1 demonstrates examples of possible embodiments based on particular requirements of parameters and allowable tolerances. These examples are meant to illustrate specific applications, and are not meant to limit the invention.

TABLE 1

Sample values and tolerances for several different embodiments of the invention.

| Parameter | Hockey | | Football | | Baseball (right-handed batter) |
|---|---|---|---|---|---|
| center thickness, mm | 3.76 | | 3.11 | | 3.76 |
| index of refraction | 1.59 | | 1.59 | | 1.59 |
| meridian | Horizontal | Vertical | Horizontal | Vertical | Horizontal & Vertical |
| front surface curvature, mm | 94.8 | 187.4 | 106.0 | 192.7 | 176.7 |
| Rear surface curvature, mm | 93.4 | 186.0 | 104.85 | 191.55 | 175.3 |
| total power, diopters | 0 | 0 | 0 | 0 | 0 |
| angle between lens optical axis (OA) and wearer's normal line of sight (NLOS) | 0 | OA 15 deg below NLOS | 0 | OA 15 deg above NLOS | OA 30 deg left of NLOS |
| total power tolerance, diopters | ±0.12 | ±0.12 | ±0.12 | ±0.12 | ±0.12 |
| separation of front and rear centers of curvature, mm | 2.36 | 2.36 | 1.96 | 1.96 | 2.36 |

An alternate or additional application could result in a different or greater angle between the shield optical axis and the wearer's normal line of sight. For example, a shield for a left-handed baseball batter could incorporate an optical axis 30 degrees to the right of the normal line of sight. Likewise, a shield for luge participants could incorporate an optical axis 45 degrees below the normal line of sight. Similarly, a shield for skeleton participants could incorporate an optical axis 40 degrees above the normal line of sight.

With the helmet in place on the wearer, and the head and eyes in the position they would assume for the nonnallines of sight, lens 50 has an apex 66 (FIGS. 2-4) which is the forwardmost point of the shield lens that would first come into contact with a frontal plane as the shield lens approaches the frontal plane when the head is held in an upright or neutral position. The frontal plane is perpendicular to the normal straight-ahead lines of sight; hence the frontal plane FP is a vertical plane, which is shown in FIGS. 3-4 tangent to the apex of the lens, where the apex 66 of the lens is located below the lines of sight, and halfway between the lines of sight. In this embodiment, the shield has reverse (or negative) pantoscopic tilt. In other embodiments, the shield may have positive or even no pantoscopic tilt. Pantoscopic tilt (either forward or reverse) can be used to improve face coverage, clearance and fit. However, regardless of any tilt that is chosen, the optical center OC will for example be below the apex in a hockey shield which is worn by a player looking down toward the ice rink surface, or above the apex for a skeleton participant lying prone who is looking toward an upper edge of the shield while participating in competition. The optical center is displaced from the apex in the same direction that the activity specific line of sight is displaced from the normal straight ahead line of sight. Hence in a shield to be worn for an activity specific line of sight that is up and to the right from the nonnalline of sight, the optical center of the shield is displaced up and to the right of the apex of the shield. The distance by which the optical center is displaced in this manner is preferably proportional to the distance by which the activity specific line of sight is displaced from the nonnalline of sight, although non-proportional displacement can also achieve a degree of noticeable optical correction.

As illustrated in the embodiment of FIG. 3, the vertical centers of curvature $\mathbf{54}_v$, $\mathbf{58}_v$ are arranged with respect to one another such that optical axis 62 extends through them at an angle $\theta_v$ to the normal line of sight 60. The direction of deviation of optical axis 62 away from the normal line of sight 60, and the value of angle $\theta_v$, depends on the particular use for which the shield is intended. In some embodiments, optical axis 62 is downwardly inclined below the plane of the normal line of sight 60 (the plane through sight line 61 that includes the normal lines of sight of both eyes), for example at or below apex 66. The optical center is the point at which the optical axis intersects the lens, or intersects an imaginary (virtual) extension of the lens. Displacement of the optical center away from the apex is referred to as optical decentration, and such optical decentration can occur either in the horizontal plane (for example toward or away from the nose), in the vertical plane (for example toward the top of the head or the chin), or in both planes (for example an optical center at the bottom lateral edge of the lens).

For the hockey shield illustrated in FIGS. 1-5, optical axis 62 extends in the vertical midline of the lens (a vertical line of symmetry of the lens) but is inclined downwardly to the plane of the normal line of sight 60 by an angle of about (or at least) 15 degrees with respect to the normal line of sight, such that it is below apex 66, and does not even intersect lens 50 but instead extends below lower edge 26 of lens 50. This arrangement provides an optical center 68 that is located on an imaginary extension of lens 50, below lower edge 26. In this position, the optical center will produce minimal image shift as the wearer's line of sight moves from below lens 50 and into the lens itself. The reduction of the image shift is of particular advantage for someone who shifts a line of sight between normal line of sight 60 and an activity specific line of sight below shield 10 (such as a line of sight a hockey player may use to view a puck on the surface of an ice rink).

In use, helmet 12 is placed on the head of a wearer, with the shield in the closed position so that lens 50 extends over and protects the eyes and nose of face 16 in the as worn orientation of the shield. Vents 36*a*, 36*b*, 36*c* and 36*d* provide for air circulation through the space between face 16 and shield 10 to help minimize fogging of lens 50. Shield 10 can also be rotated to an open position by lifting up its lower edge 26 to pivot lens 50 away from the face around hinges 40*a*, 40*b*.

When shield 10 is in the closed position, a hockey player is able to shift gaze from looking through the lens to below the lens, while minimizing image shift that occurs as the line of sight passes over this interface. The amount of image shift will be proportional to the distance between the sight specific line of sight (such as looking at a hockey puck on the surface of an ice rink) and the position of the optical center. Hence an optical center positioned below the lower edge of lens 50 will produce substantially less image shift than similar lenses in which the optical center is located at the apex, or at the level of the NLOS.

Although the particular example illustrated in the drawings is a hockey shield, the principles of the invention can be extended to many other types of shields to minimize the spatial distortion when the activity specific line of sight is located on the lens but not coincident with the normal line of sight, as well as the image shift that occurs when the line of sight crosses from the lens edge. For example a surgeon may have a protective face mask that covers the eyes and nose but not the rest of the face. In those instances in which the primary visual activity for the surgeon is toward the lower edge of the shield, and in some cases when the line of sight shifts between the lens and below it, optical advantages are provided by vertical decentration of the lens to or below the lower edge of the lens. Particular examples of decentration along a vertical midline include a decentration of at least 10, 20 or 30 mm from the lens apex. Decentration of this or any other lens may occur either in the vertical midline of the lens (halfway between the two lines of sight), or away from the vertical midline of the lens.

In another example, the optical center may also be horizontally decentered, such that it is not equidistant between the two eyes. This type of shield may be intended for use with laterally-displaced specific activity lines of sight, such as baseball batting and short-track speed skating. A baseball batter, for example, stands somewhat sideways to the path of a thrown baseball with the head at an angle that results in a sideways gaze, and often an upward gaze as well. The horizontally decentered optical center may be, for example, nearer the activity specific line of sight toward which the direction of gaze is directed. For example, if the activity specific line of sight is laterally displaced toward the right of the NLOS, then the optical center may be positioned closer to the activity specific line of sight of the right eye than the left eye (and in certain embodiments the optical center may even be coincident with the activity specific line of sight of the right eye).

In yet another example, a football player will have an activity specific line of sight predominantly in an upward direction, such that the optical center may be near or above the upper edge of the shield. Such an upward line of sight would be used, for example, when standing in formation prior to a play. Different players in a game (such as defensive linemen and wide receivers in a football game) may have different activity specific lines of sight, such that different shields are suitable for different players on the same team. The activity specific lines of sight for a particular game (or for participants in a game who are performing a function) may be determined for each individual player or fixed for a particular game or class of player.

In yet other examples, the activity specific line of sight is both vertically and horizontally displaced from the normal line of sight, such that the optical center is both vertically and horizontally displaced from the apex of the shield. In disclosed embodiments, the optical axis is horizontally and vertically displaced from the NLOS and the ASLS, and substantially parallel to the ASLS (for example, within 5 or 10 degrees of parallel). In specific embodiments, the optical axis is substantially equidistant between the ASLS of the right and left eyes but in other embodiments is not equidistant therebetween. For example, the optical axis (and optical center) may be vertically displaced from the apex in a direction that corresponds to a vertical component of gaze, in that the optical axis is displaced downwardly from the apex if the direction of gaze is downward from the NLOS. Similarly, the optical axis may be between the ASLS of the right and left eyes, but closer to the eye toward which a horizontal component of gaze is directed. Alternatively, the optical axis may be coincident with the ASLS of the eye toward which the horizontal component of gaze is directed, or have shifted beyond the ASLS of the eye toward which the horizontal component of gaze is directed, so that the optical axis is no longer between the ASLS of the right and left eye. For example, if the direction of gaze has a horizontal component that is directed toward the left, then the optical axis is closer to the ASLS of the left eye than the ASLS of the right eye. In particular examples, the optical axis may be between the ASLS of the right and left eye, coincident with the ASLS of the left eye, or shifted beyond the ASLS of the left eye such that the optical axis is not between the ASLS of the right and left eye.

Designing Shield with Specific Lens Power and Pantoscopic Tilt

By convention, the curvature of the front surface of a lens is called the base curve and is defined as 530/$R_1$, where $R_1$ is the radius of curvature of that surface in millimeters. A line through the centers of curvature $C_1$ (of the front surface) and $C_2$ (of the rear surface) defines an optical axis OA that intersects the lens (or an imaginary extension of the lens) at an optical center OC. The lens (or its imaginary extension) has a thickness CT along the optical axis OA, and tapers symmetrically away from or towards the optical center OC (depending on the power of the lens). The radius of curvature $R_2$ of the rear surface is selected in combination with the center thickness CT and the base curve radius $R_1$ to provide a predetermined lens power. The radius $R_2$ for a selected lens power P is readily calculated using the standard formula for lens power:

$$P=(n-1)\left[\frac{1}{R_1}-\frac{1}{R_2}+\frac{(n-1)CT}{n\,R_1R_2}\right]$$

wherein n is the refractive index of the lens material.

Pantoscopic tilt may be defined as the angle between the apex plane (the FP shown in FIGS. 3 and 4, which is perpendicular to the normal lines of sight of the right and left eyes) and the tangent to the lens surface at the intersection of the lens surface and the nonnalline of sight. The shield disclosed herein can have pantoscopic tilt (inclined toward the face), reverse pantoscopic tilt (inclined away from the face), or no pantoscopic tilt. Depending on the amount and direction of pantoscopic tilt and the horizontal and vertical dimensions of the shield, the apex may be present on the lens surface or it may be off the lens surface, such that it can be located by virtual extension of the lens surface.

Determining Activity Specific Line of Sight (ASLS)

The line of sight will often change depending on the task a person is performing. This task specific line of sight is referred to herein as an activity specific line of sight (ASLS). The ASLS is the line along the fixation axis of the eye when the eye and head are directed in a preferred position for performing a particular visual function or task (e.g. playing ice hockey, trail running, volleyball, surgery, baseball batting, or driving). In trail running, for example, the eye may be rotated such that the visual fixation axis through the center of the pupil is lowered about 15 degrees below the normal straight ahead line of sight. Although the visual fixation axis for different activities is not always constant, there is a preferred line of sight that is adopted for specific activities, and for which a lens can be designed.

There are several approaches to determining the ASLS. A population of persons performing a task can be observed performing the task, and each of their lines of sight marked on the lenses of eyewear or shields they are wearing (or photographs taken of the pupils through the lenses) to arrive at a norm for the ASLS. Alternatively, infrared pupil position detectors can be worn by persons performing the tasks, and the pupil positions determined remotely. In addition, video analysis of head and body position can be performed. The ASLS can be determined for an individual (if a custom protective shield is being made), or an average position of the ASLS can be determined for a population of persons who perform the activity. The lens or shield can then be worn by persons performing the function for which the lens or shield is designed, and refinements made to the position of the optical axis based on the visual performance and comfort of the wearer. Since the eyes may converge as part of an accommodative reflex if the activity involves closer activity, the plane of the ASLS can be determined as a reference plane that includes the ASLS of the right and left eyes (referred to herein as the ASLS plane). In examples in which the ASLS is straight up or straight down from the neutral straight ahead position, the optical center OC is preferably placed equidistant between the lines of sight of the two eyes.

The ASLS can be in the vertical midline of the shield (substantially equidistant between the eyes), or away from that vertical midline (toward one of the eyes). The ASLS can also be above or below the plane that contains the nonnallines of sight of the wearer. In particular embodiments, the ASLS is both horizontally and vertically displaced from the normal straight ahead line of sight.

Once the angle between the ASLS (or the ASLS plane) and the normal straight ahead line of sight (or the plane that contains both NLOS) is determined for the particular sport or activity, whether for an individual or a population, this sets the angle between the optical axis of the shield and its apex (when the head and eyes are in a position that would define the nonnalline of sight).

In particular embodiments, the shield has a functional apex defined by the tilt of the head and body position of the wearer. A functional apex is a forwardmost point on a lens that first touches a plane advancing toward the shield perpendicular to the functional line of sight.

Placement of Optical Center

In many embodiments it is useful for the optical center to be on a vertical meridian of the lens, halfway between the straight ahead lines of sight of the two eyes. Hence for an example in which the activity specific line of sight is straight down from the normal straight ahead line of sight, the optical center is decentered downward the same angle as the activity specific line of sight and the decentration occurs along the vertical meridian, such that the horizontal offset of the optical center from each line of sight is substantially equal for both eyes. In other embodiments in which both horizontal and vertical decentration is desired to accommodate an activity specific line of sight, for example, which may be down and to the right, or up and to the left, the decentration moves the optical center in the same direction as the activity specific line of sight, along both the vertical and lateral meridians. In particular examples, the position of the dec entered optical axis remains substantially parallel to the activity specific line of sight of each eye, and is either substantially equidistant between the ASLS of each eye (for example when the ASLS is either straight up or down from the NLOS) or closer to the ASLS of the right or left eye (for example when the ASLS is directed laterally from the NLOS). In certain examples in which the ASLS is directed laterally from the NLOS, the optical axis is closer to (including coincident with) the ASLS of the eye toward which the ASLS is directed (for example closer to the ASLS of the right eye if the ASLS is laterally directed toward the right). As used herein, references to right, left, up and down are the directions with reference to the person who is wearing the shield.

Figure 6A:
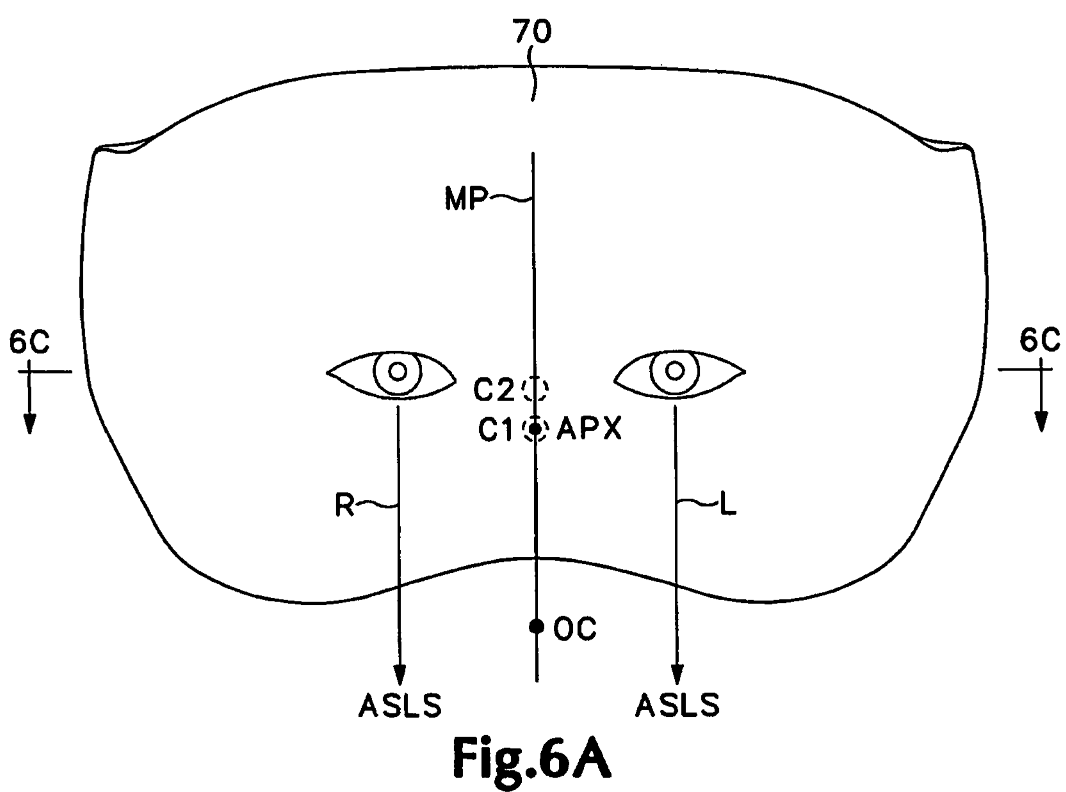
FIG. 6A illustrates a schematic front view of the shield.
Figure 6B:
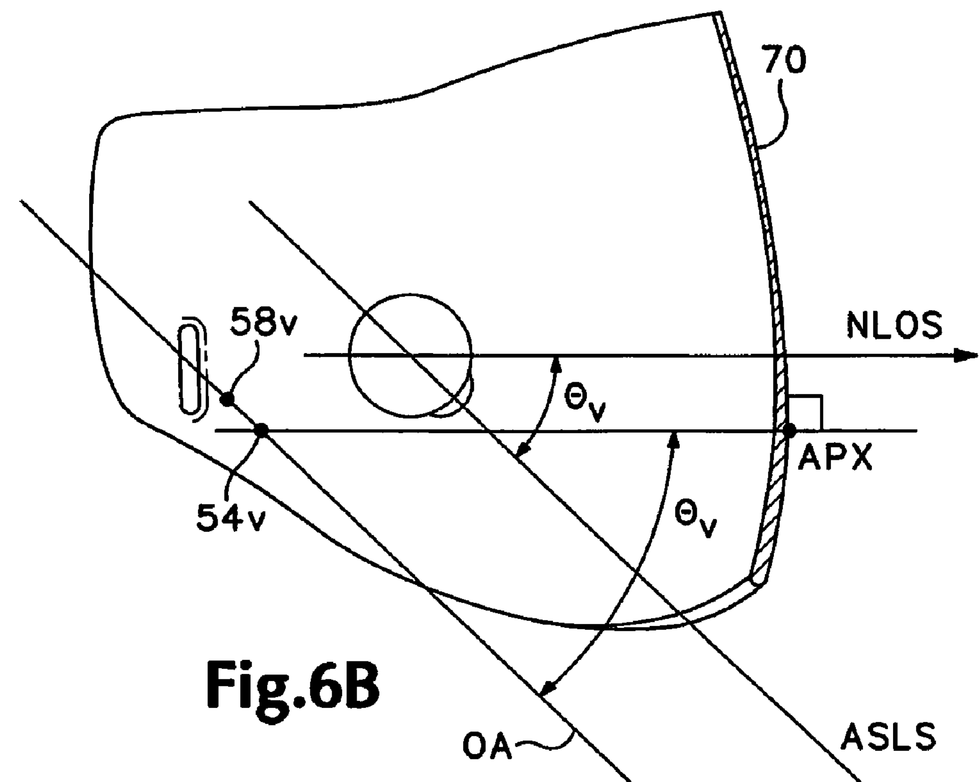
FIG. 6B is a side view of the shield shown in FIG. 6A.
Figure 6C:
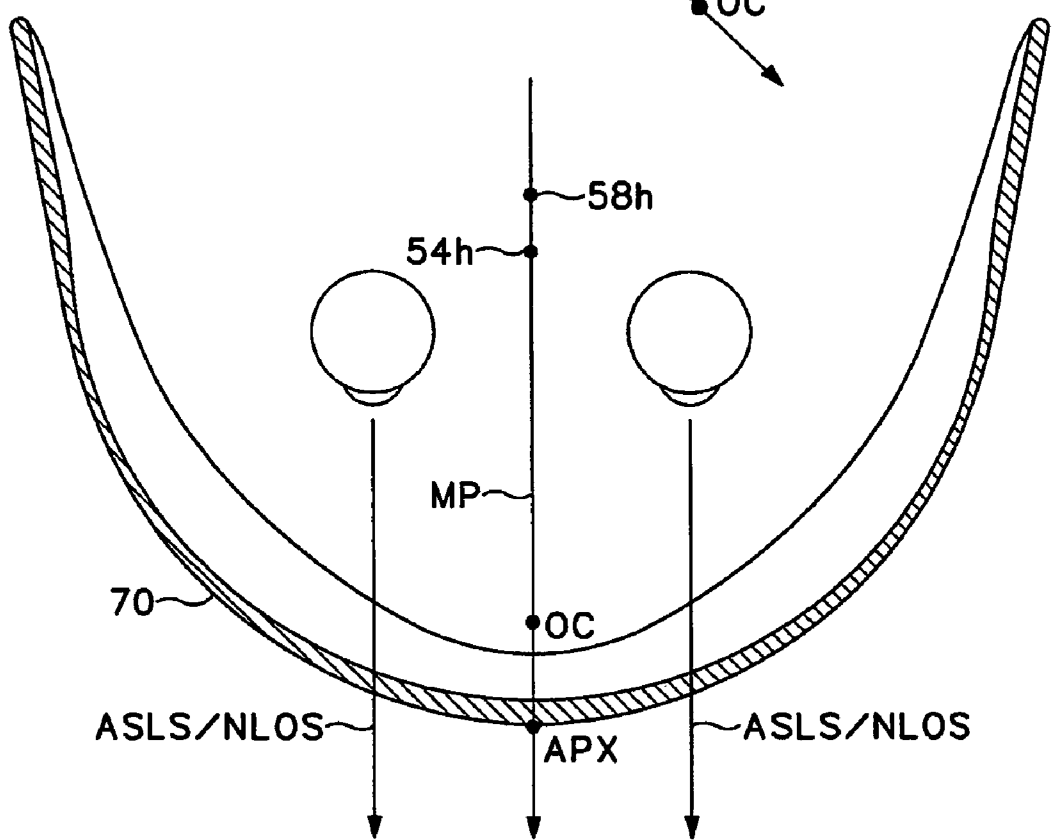
FIG. 6C is a horizontal section through the shield of FIG. 6B at the level of the NLOS along lines 6C-6C. The displacement of the activity specific line of sight (ASLS) from the normal line of sight (NLOS) and apex (APX) is depicted by arrows in FIG. 6A

Some additional examples of decentration for different activity specific lines of sight in a shield 70 are shown in FIGS. 6-9, which help illustrate the horizontal and vertical placement of the optical center in these situations. FIG. 6, for example, shows an activity specific line of sight that is displaced directly vertically downward, without substantial deviation to the right or left. The direction of displacement of the visual axis is shown schematically in FIG. 6A by the downwardly pointing ASLS arrows R (for the right eye) and L (for the left eye). If the activity specific line of sight (ASLS) is broken into a horizontal and a vertical component, the vertical component of the ASLS is displaced downwardly (as shown in FIG. 6B) at an angle $\theta_v$ to the normal straight ahead line of sight (NLOS) and the horizontal component (shown in FIG. 6C) remains substantially parallel (for example within ±5 degrees, for example within ±2 degrees) to the NLOS. In this situation, the lens is designed with the optical center OC in the median plane MP substantially equidistant between the NLOS of each of the right and left eyes. The median plane may, in some examples, be a vertical plane that bisects the shield into symmetric halves. In FIG. 6, the optical axis OA extends through an optical center at point OC that is in the median plane, on an imaginary extension of the shield, such that the horizontal angle of deviation of the optical axis is at an angle $\theta_h$ of substantially zero to the NLOS, and the vertical component of the optical axis is at the angle $\theta_v$ to the NLOS. The angle of downward angular deviation may be, for example, 5-15 degrees or more from the straight ahead nonnalline of sight (NLOS). The optical axis extends through centers of curvature $\mathbf{54}_v$ and $\mathbf{58}_v$ in the median plane (as shown in FIG. 6B) to provide the vertical curvature of the shield lens, and through the centers of curvature $\mathbf{54}_h$ and $\mathbf{58}_h$ in the horizontal (as shown in FIG. 6C) to provide the horizontal curvature of the shield lens. As previously noted, the centers of curvature may be different for the vertical and horizontal curvatures of the lens for a non-spherical lens, but for purposes of simplification a front center of curvature ($C_1$) and a rear center of curvature ($C_2$) are illustrated in FIG. 6A.

The apex APX is also shown in FIG. 6. As already noted (and shown in the drawing), the apex APX is the forwardmost point of the shield when the shield is mounted in front of the eyes in the as worn orientation, with the head upright. Also, the line perpendicular to the front surface at the apex APX, or apex line, is parallel to the nonnallines of sight of both eyes and intersects front vertical center of curvature $54_v$. Consequently, the downwardly inclined optical axis OA will intersect both the apex line and the nonnalline of sight with the same angle (as shown in FIG. 6B). FIGS. 6A-6C show that the optical axis of the shield is decentered by displacement of the optical center from the apex APx. In the disclosed example, the optical center OC is decentered only vertically downward from the apex APX, while remaining in the median plane MP. In particular examples, the optical center OC is moved vertically downward from the apex APX by 10 to 30 mm, for example 20 mm. The illustrated optical axis OA is spaced from and substantially parallel to each ASLS (and the ASLS plane) In this example, optical axis OA is displaced downwardly from the ASLS plane, but is equidistant between the ASLS of each eye and extends in the median plane MP.

Figure 7A:
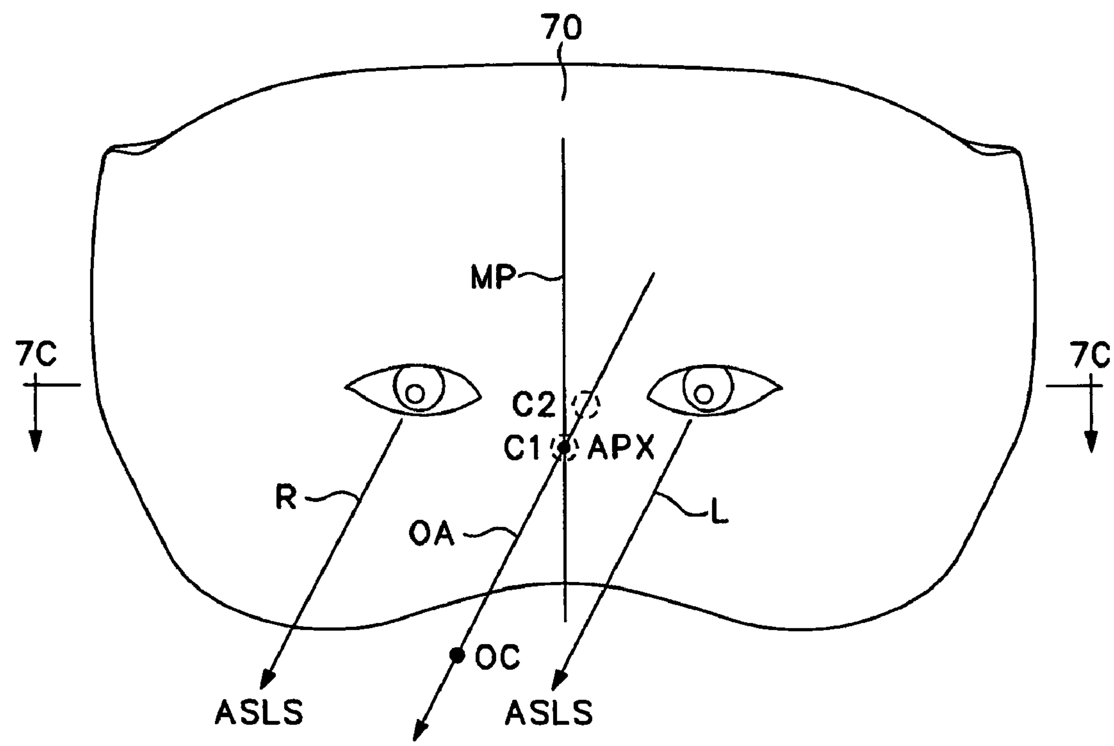
FIGS. 7A-7C are schematic drawings similar to FIGS. 6A-6C, but illustrating horizontal and vertical decentration in a shield designed for an activity specific line of sight (ASLS) that is displaced down and to the right from a normal straight ahead line of sight (NLOS) and apex (APX).
Figure 7B:
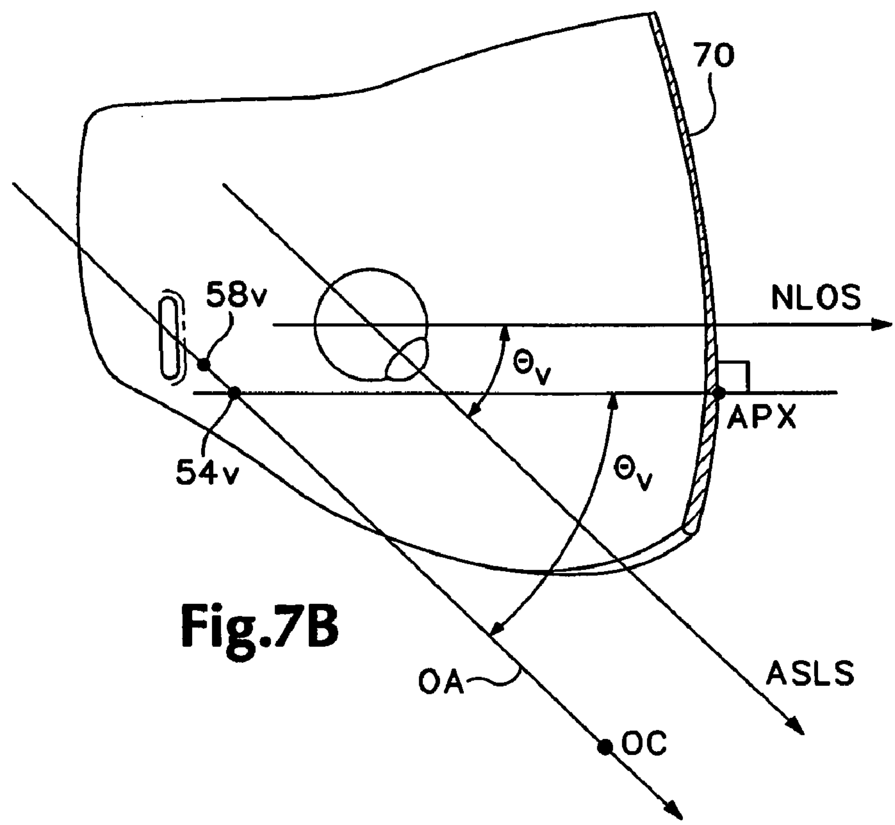
Figure 7C:
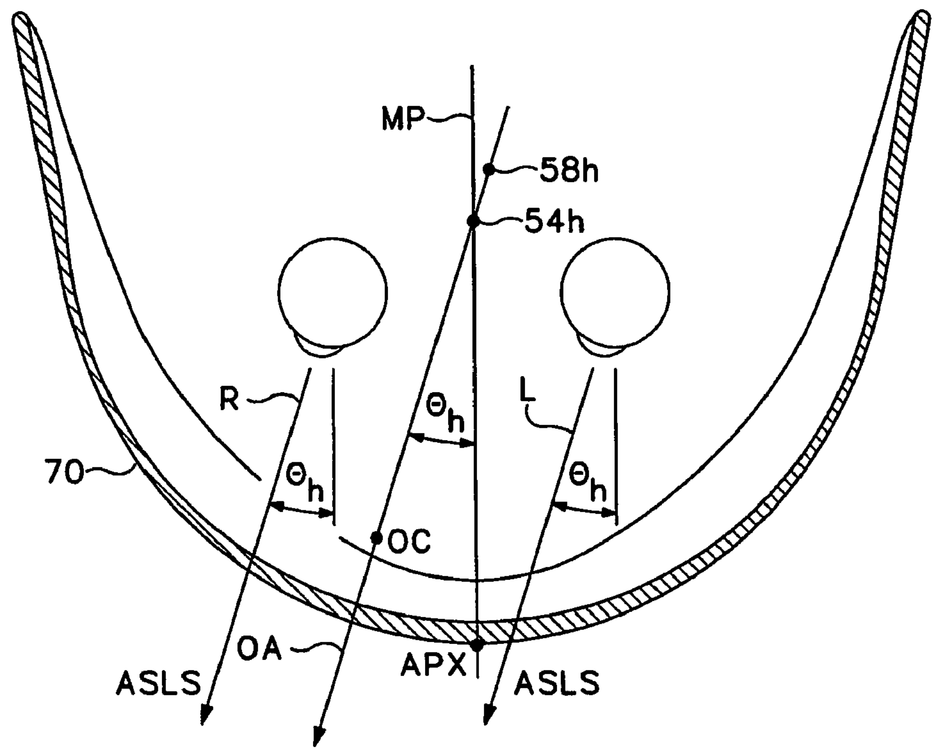

FIG. 7 illustrates an ASLS in which the visual axis of each eye is both depressed below the NLOS and deviated to the wearer's right. The direction of displacement of the visual axis is shown schematically in FIG. 7A by the arrows R (for the right eye) and L (for the left eye) that are pointing down and to the right. If the activity specific line of sight (ASLS) is broken into horizontal and vertical components, the vertical component of the ASLS (shown in FIG. 7B) is displaced downwardly at an angle $\theta_v$ to the NLOS and the horizontal component (shown in FIG. 7C) is displaced horizontally at an angle of $\theta_h$ to the normal straight ahead line of sight. The optical axis (which extends through the centers of curvature $C_1$, with components $54_h$ and $54_v$, and $C_2$, with components $58_h$ and $58_v$, of the shield lens 70) is similarly angled vertically to both the normal line of sight plane and the apex line by an angle $\theta_v$ that is the same as the vertical component of the angle of deviation of the ASLS from the NLOS (FIG. 7B), and angled horizontally to both the median plane and the apex line by the angle $\theta_h$ that is the same as the horizontal component of the angle of deviation of the ASLS from the NLOS. In FIG. 7, the optical axis extends through centers of curvature $C_1$ and $C_2$, and through an optical center at point OC that is to the right of the median plane MP of the shield, on an imaginary extension of the shield, and below the lower edge of the shield. The angle of downward displacement $\theta_v$ may be, for example, 5-15 degrees or more, and the angle of horizontal displacement $\theta_h$ may similarly be 5-15 degrees or more. The optical center is also moved away from the apex APX in the same directions (down and to the right) as the direction of deviation of the ASLS from the NLOS. In particular examples, the downward displacement of the optical center OC from the apex APX is 10-30 mm, and the lateral displacement is 10-30 mm from the apex APK.

The vertical placement of the OA can be determined, for example, by drawing the OA substantially parallel to each ASLS, through the front center or centers of curvature of the shield. Hence for the vertical curvature (FIG. 7B), the OA placement is determined by orienting the OA substantially parallel and spaced from the ASLS plane, with the OA extending through point 54*v*. For the horizontal curvature, the OA placement is determined by orienting the OA substantially parallel and spaced from each ASLS, with the OA extending through point 54*h*. The positions of the rear centers of curvature (58*v*, 58*h*) can be positioned to achieve this orientation of the OA, while keeping the front centers of curvature (54*v*, 54*h*) fixed.

Figure 8A:
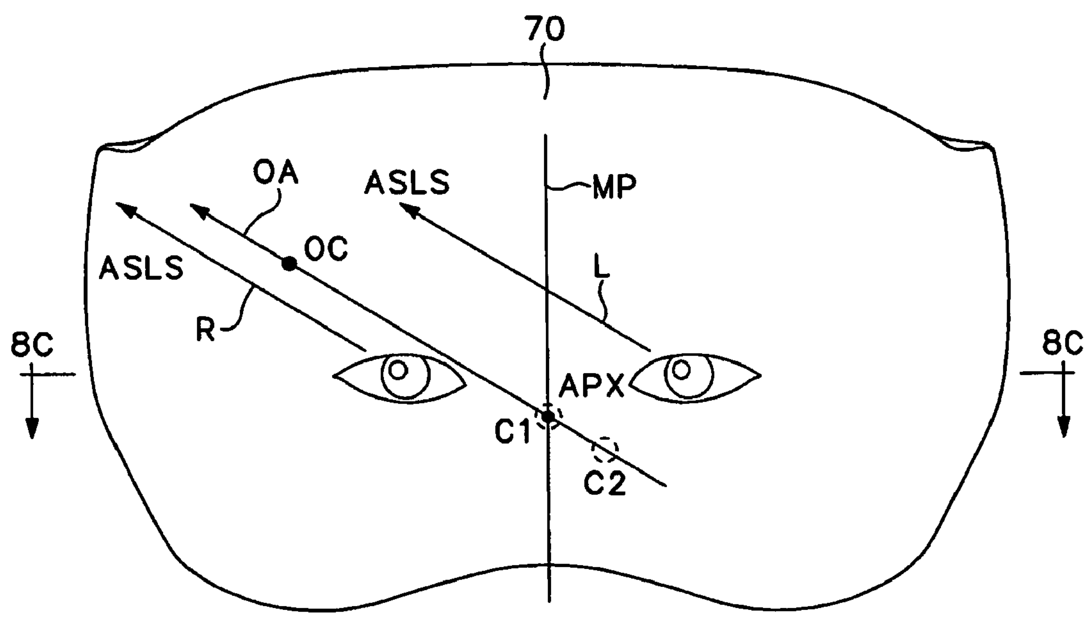
FIGS. 8A-8C are schematic drawings similar to FIGS. 6A-6C, but illustrating horizontal and vertical decentration in a shield designed for an activity specific line of sight (ASLS) that is displaced up and to the right from a normal straight ahead line of sight (NLOS) and apex (APX).
Figure 8B:
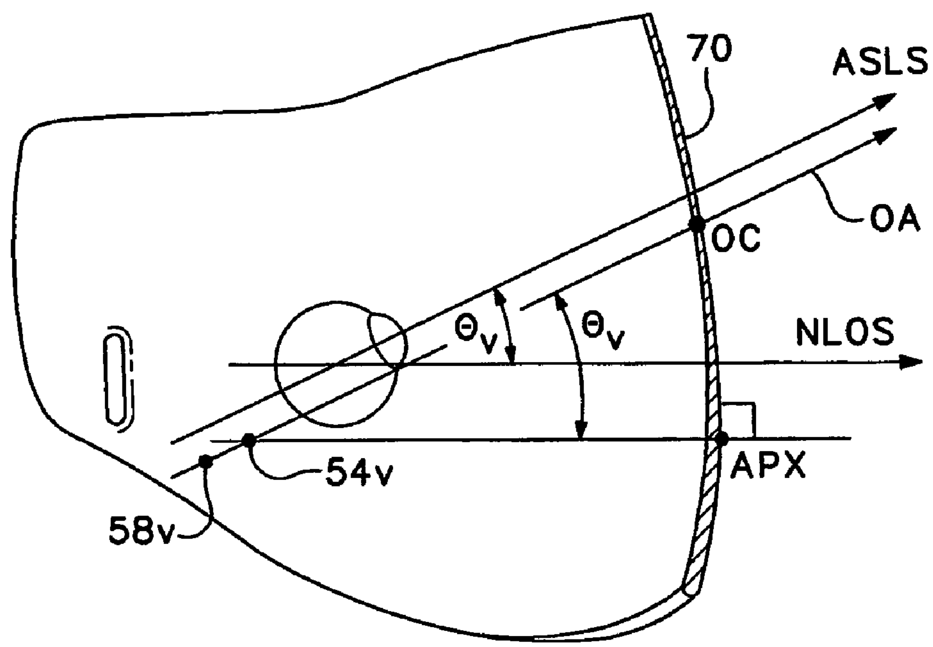
Figure 8C:
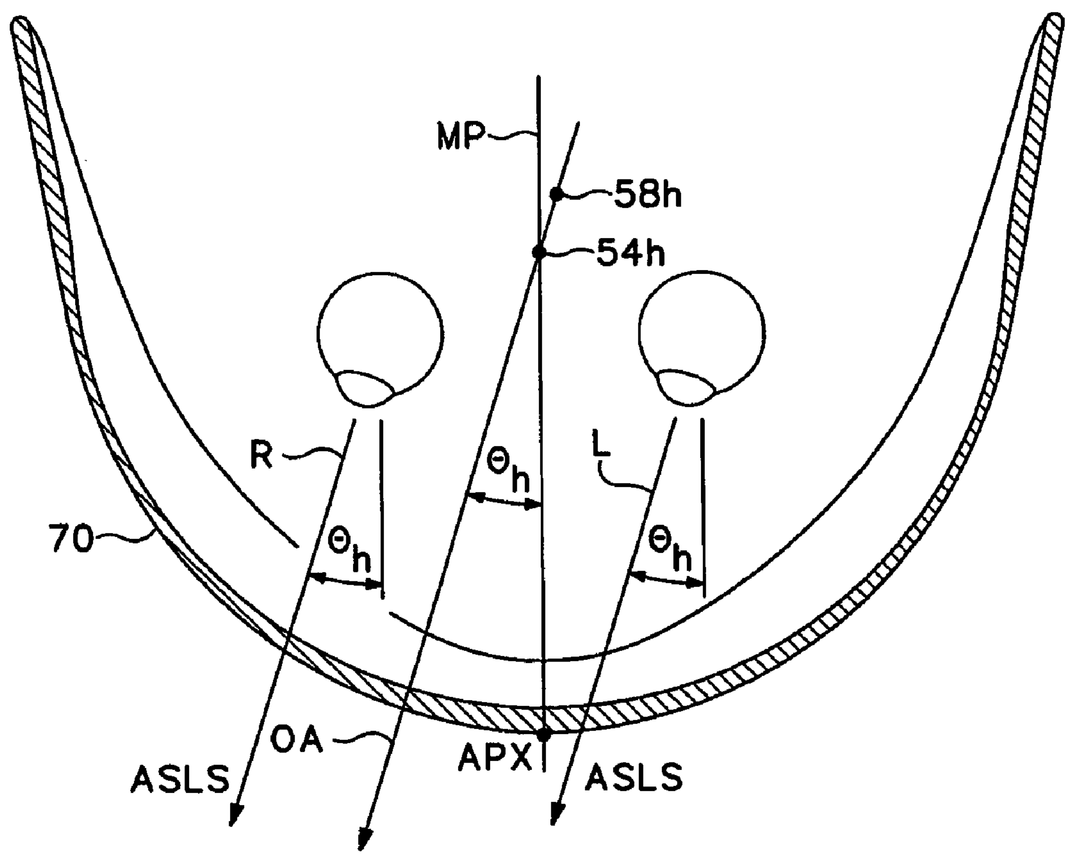

FIG. 8 illustrates an ASLS in which the visual axis of each eye is both elevated above the NLOS and deviated to the wearer's right. The direction of displacement of the visual axis is shown schematically in FIG. 8A by the ASLS arrows R (for the right eye) and L (for the left eye) that are pointing up and to the right. If the activity specific line of sight (ASLS) is broken into a horizontal and a vertical component, the vertical component of the ASLS (shown in FIG. 8B) is displaced upwardly at an angle $\mathbf{8}_v$ to the NLOS and the horizontal component (shown in FIG. 8C) is displaced horizontally at an angle of $\mathbf{8}_h$ the normal straight ahead line of sight. The optical axis OA is also angled vertically to both the normal line of sight plane and the apex line by an angle $\theta_v$ that is the same as the vertical component of the angle of deviation of the ASLS from the NLOS (FIG. 8B), and angled horizontally to both the median plane MP and the apex line by the angle $\theta_h$ that is the same as the horizontal component of the angle of deviation of the ASLS from the NLOS. In FIG. 8, the optical axis extends through an optical center at point OC that is to the right of the median plane MP of the shield, above the equator of the lens, but below the upper edge of the shield. The angle of upward displacement $\theta_v$ may be, for example, 5-15 degrees or more, and the angle of horizontal displacement $\theta_h$ may similarly be 5-15 degrees or more. In certain embodiments, the optical center OC is above the top edge of the shield lens. The optical center OC is displaced in the same directions (up and to the right). In particular examples, the upward displacement of the optical center OC from the apex APX is 10-30 mm, and the lateral displacement is 10-30 mm from the apex APX.

FIG. 8 also illustrates that the OA is horizontally and vertically spaced from, and substantially parallel to, the ASLS plane. The OA shifts closer to the ASLS (while remaining substantially parallel to it) proportional to an increasing angle of vertical deviation of the ASLS to the NLOS. The OA may be, for example, between the NLOS and ASLS, coincident with or at the same level as the ASLS, or above the ASLS. Similarly, the OA moves closer to the ASLS of the right eye than the left eye (while still substantially parallel to the ASLS of both eyes) since the direction of gaze is shifted to the right. The OA moves closer to the ASLS of the right eye proportional to the increasing horizontal angle of the ASLS from the NLOS, and may be coincident with the ASLS of the right eye or to the right of the ASLS of the right eye, depending on how large the horizontal angle is between the NLOS and the ASLS. If the direction of gaze were directed to the left from the NLOS, then the OA would move closer to the ASLS of the left eye proportional to an increasing angle between the ASLS and the NLOS, while maintaining its substantially parallel spaced relationship from the ASLS. The ASLS may be coincident with the ASLS of the left eye or to the left of the ASLS of the left eye, depending on how large the horizontal angle is between the NLOS and the ASLS.

Figure 9A:
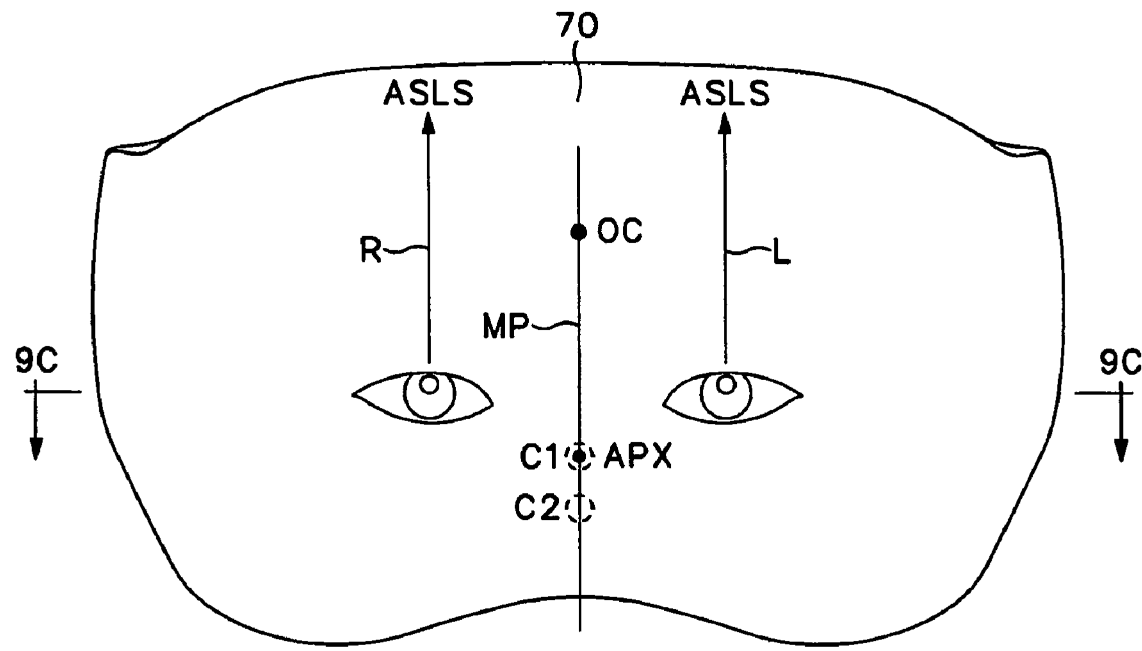
FIGS. 9A-9C are schematic drawings similar to FIGS. 6A-6C, but illustrating vertical decentration without horizontal decentration in a shield designed for an activity specific line of sight (ASLS) that is displaced only upwardly from the normal straight ahead line of sight (NLOS) and apex (APX).
Figure 9B:
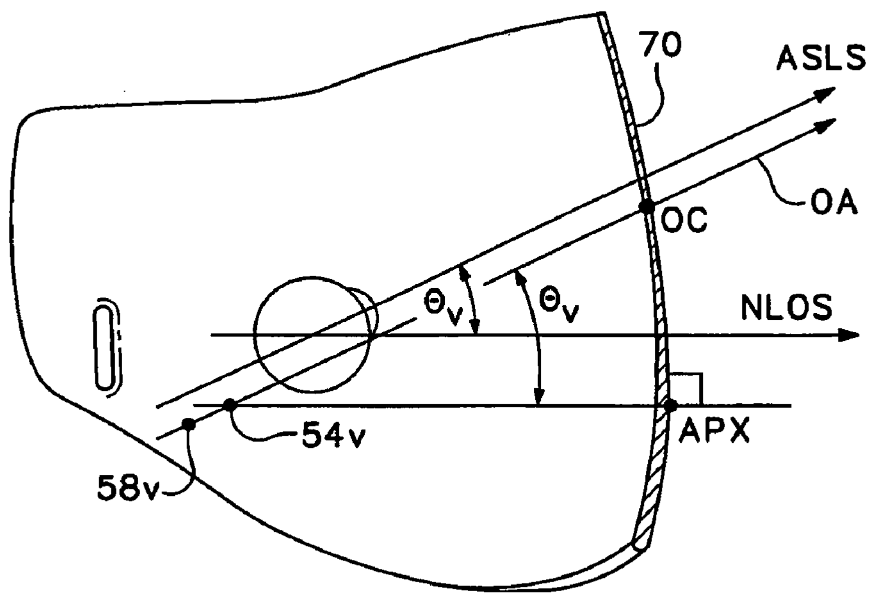
Figure 9C:
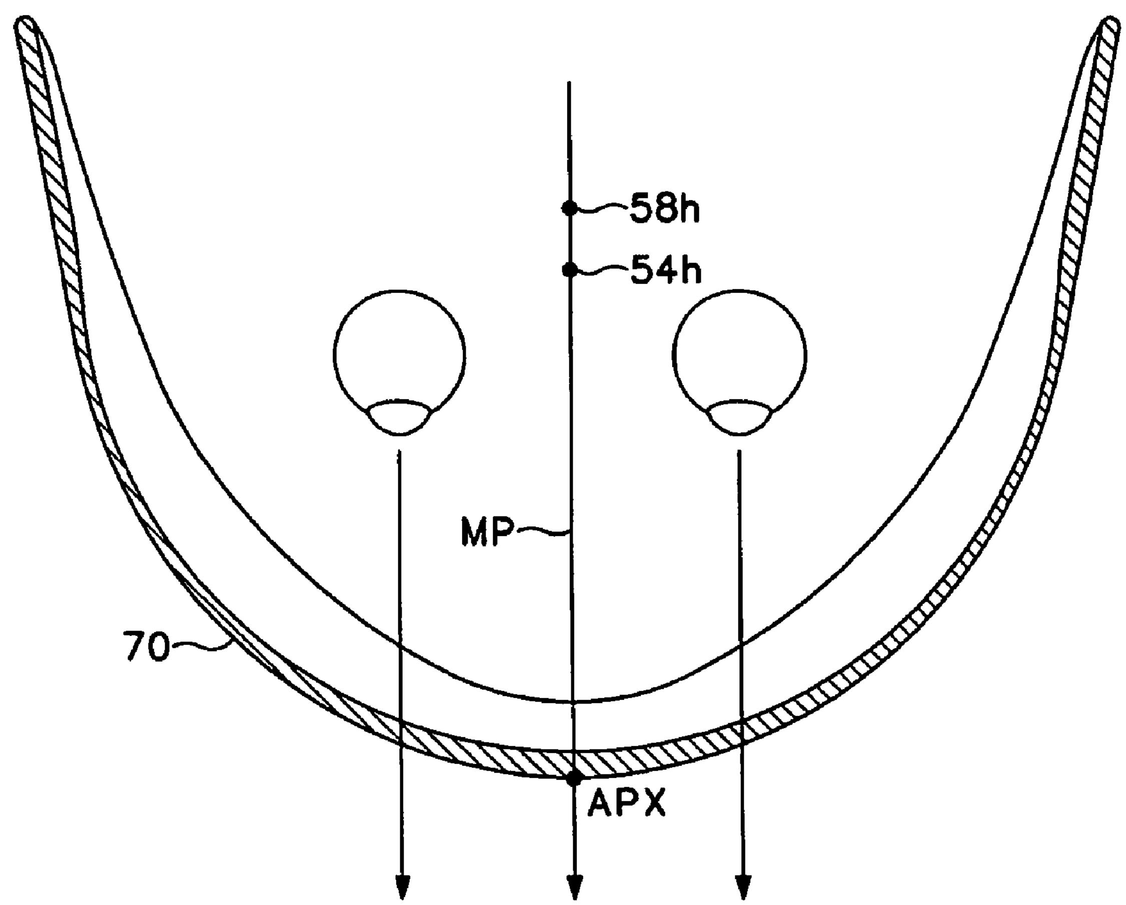

FIG. 9 shows an activity specific line of sight that is displaced directly vertically upward, without deviation to the right or left, but in which the ASLS extends through the shield and not above it. The direction of displacement of the visual axis is shown schematically in FIG. 9A by the upwardly pointing arrows R (for the right eye) and L (for the left eye). If the activity specific line of sight (ASLS) is broken into a horizontal and a vertical component, the vertical component of the ASLS is displaced upwardly (as shown in FIG. 9B) at an angle $\theta_v$ to the normal straight ahead line of sight (NLOS) and the horizontal component (shown in FIG. 9C) remains substantially parallel (within ±5 degrees, for example within ±2 degrees) to the NLOS. In this situation, the lens is designed with the optical center OC in a median plane MP equidistant between the ASLS of each of the right and left eyes. The median plane MP may, in some examples, be a vertical plane that bisects the shield into symmetric halves. In FIG. 9, the optical axis OA extends through an optical center at point OC that is in the median plane MP of the shield and on the shield, such that the optical axis is at an angle $\theta_h$ of substantially zero to the median plane MP, and at the angle $\theta_v$ to both the NLOS and the apex line. The angle of upward displacement may be, for example, 5-15 degrees or more from the straight ahead line of sight (NLOS), or the normal line of sight plane that contains the NLOS of the right and left eyes. The optical center is displaced in the same direction (upward only). In particular examples, the upward displacement of the optical center OC from the apex APX is 10-30 mm.

As can be seen in the examples of FIGS. 6-9, the optical center is placed in a location such that the optical axis extends through the optical center at an angle to the NLOS plane (NLOS P), and substantially parallel to the ASLS of the right and left eyes.

Figure 10A:
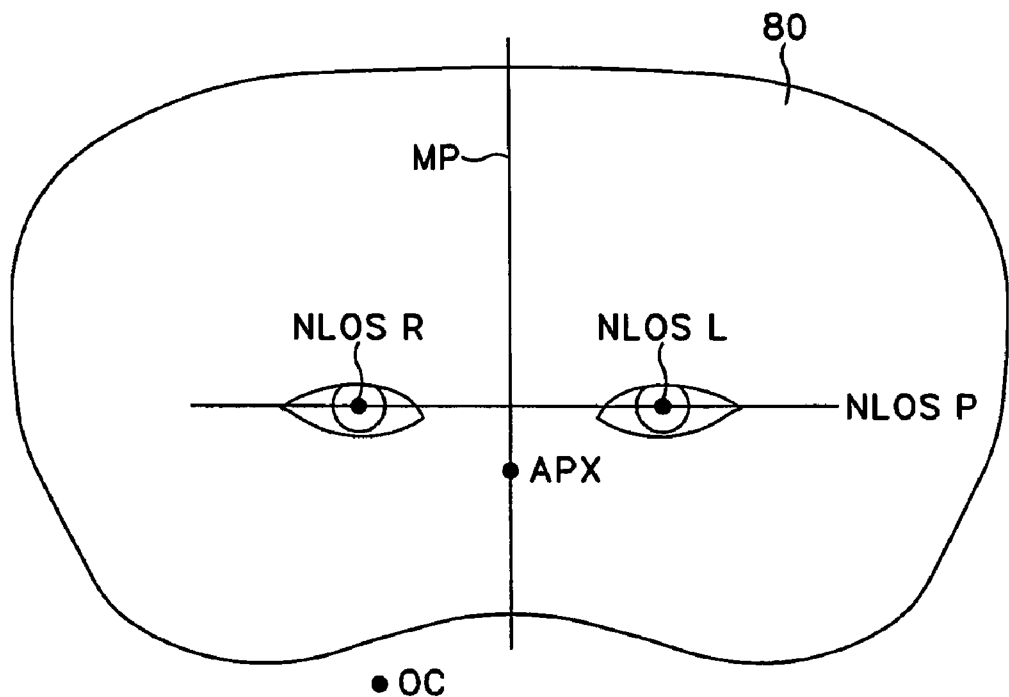
FIG. 10A is a schematic front view of a shield, illustrating a normal line of sight plane NLOS P that extends along the sight line of the shield through the plane of the normal line of sight (NLOS) of the right (NLOS R) and left (NLOS L) eye, and the median plane MP that is equidistant between the NLOS of the right and left eyes and perpendicular to normal line of sight plane NLOS P.
Figure 10B:
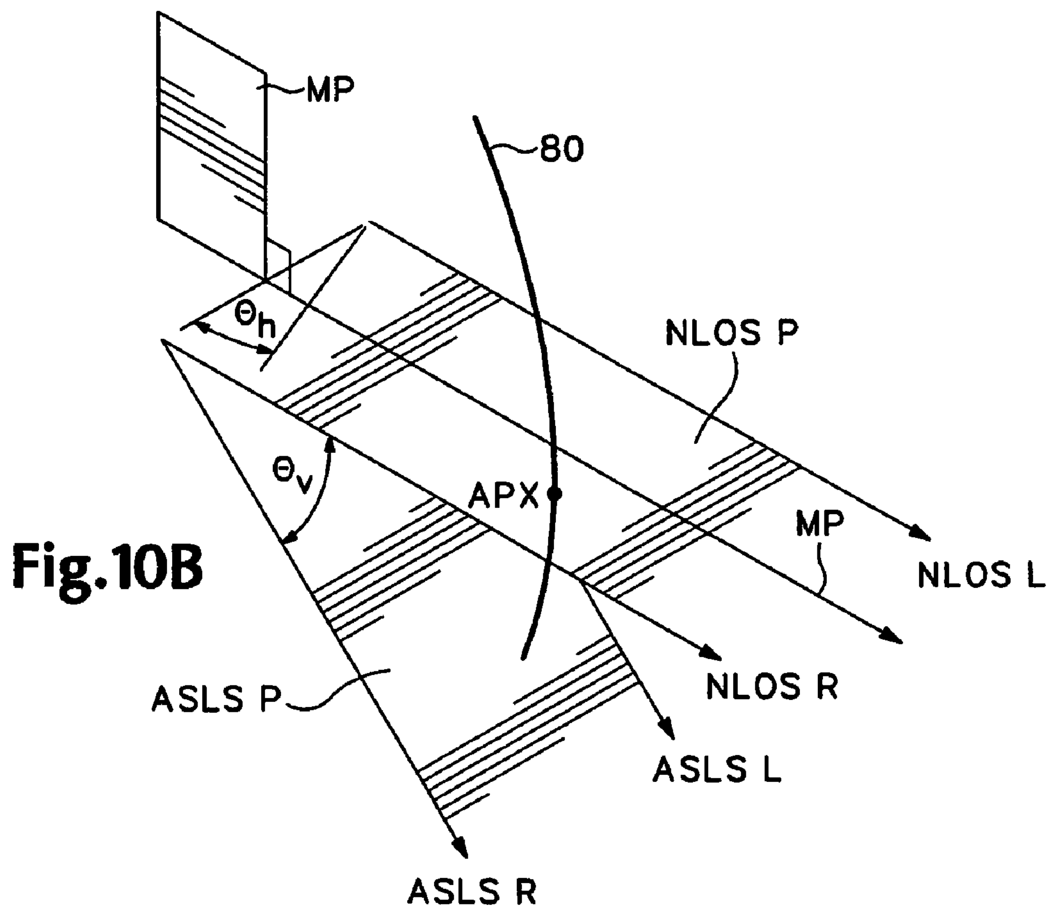
FIG. 10B is a schematic view illustrating the location of the NLOS of each eye in the normal line of sight plane NLOS P that extends through the sight line of the shield, and the location of the activity specific line of sight plane ASLS P that extends through the ASLS of the right eye (ASLS R) and the left (ASLS L) eye.

FIGS. 10A and 10B show the NLOS plane (NLOS P) that contains the NLOS of the right and left eyes, and the ASLS plane (ASLS P) that contains the ASLS of the right and left eyes. To provide a shield that compensates for the optical demands of an ASLS, the placement of the OC (and the optical axis that extends through the OC) can be determined by the deviation angle of the ASLS from the NLOS. FIG. 10B illustrates an ASLS P that has a horizontal component that is at an angle $\theta_v$ to NLOS P and a vertical component that is at an angle $\theta_h$ to the NLOS P. In certain examples, at least one of the horizontal or vertical angles $\theta_h$ or $\theta_v$ is greater than about 5 degrees, for example at least 10, 15 or 20 degrees.

Figure 10C:
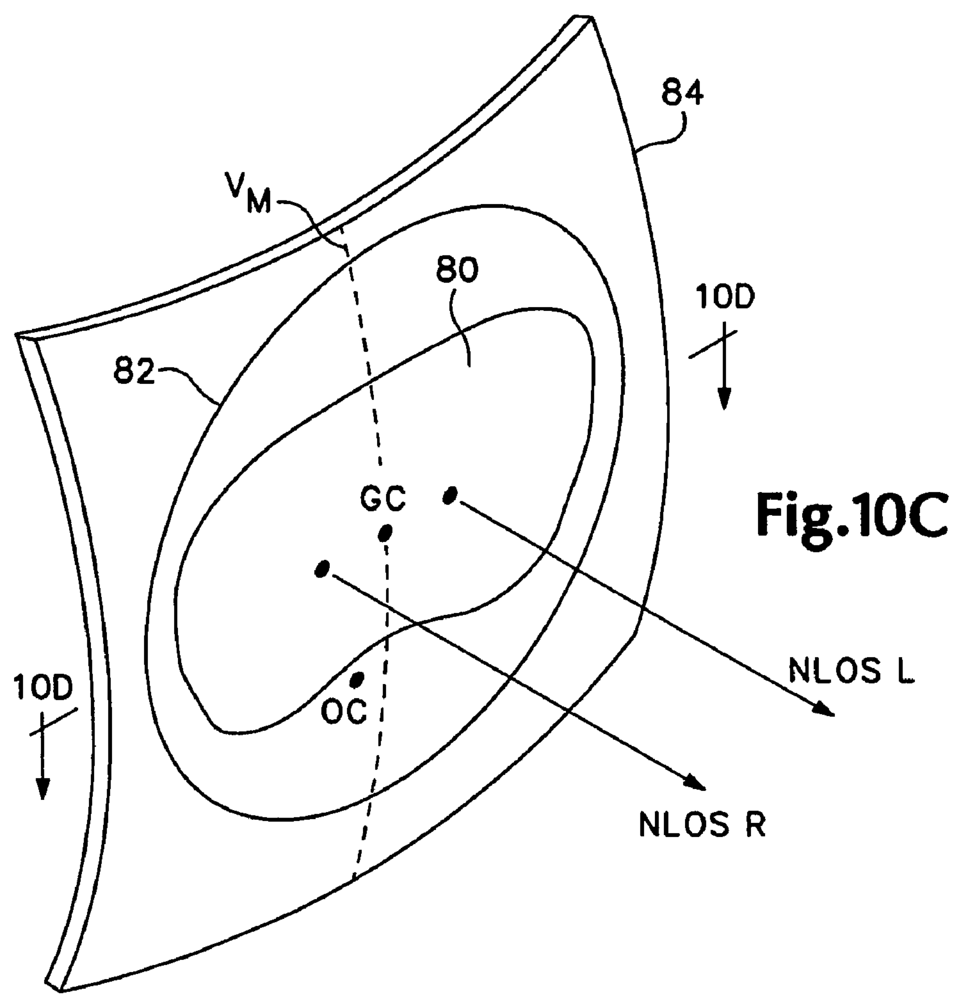
FIG. 10C is a perspective view of a lens blank conforming to a portion of a curved surface, showing a shield profile to be cut from the blank in accordance with one method disclosed herein.

FIG. 10C is a schematic view of a lens blank 82 having a circular peripheral outline conforming to a curved surface 84 from which lens blank 82 is cut. Curved surface 84 can be either spherical or toroidal, or another shape suitable for visors or shields. However, the specific surface 84 illustrated in FIG. 10C is intended to be a toroidal surface. Lens blank 82 has a geometric center GC at the center point of lens blank 82, and a vertical meridian VM bisects lens blank 82 into symmetric right and left halves. The profile of shield 80 is shown on lens blank 82, and the location of the optical center OC is positioned below the NLOS of the right eye (NLOS R), below the lower edges of the profile of shield 80, and away from the vertical meridian VM. In the illustrated embodiment, optical center OC is located to the right of vertical meridian VM (as viewed by the wearer of the shield).

Figure 10D:
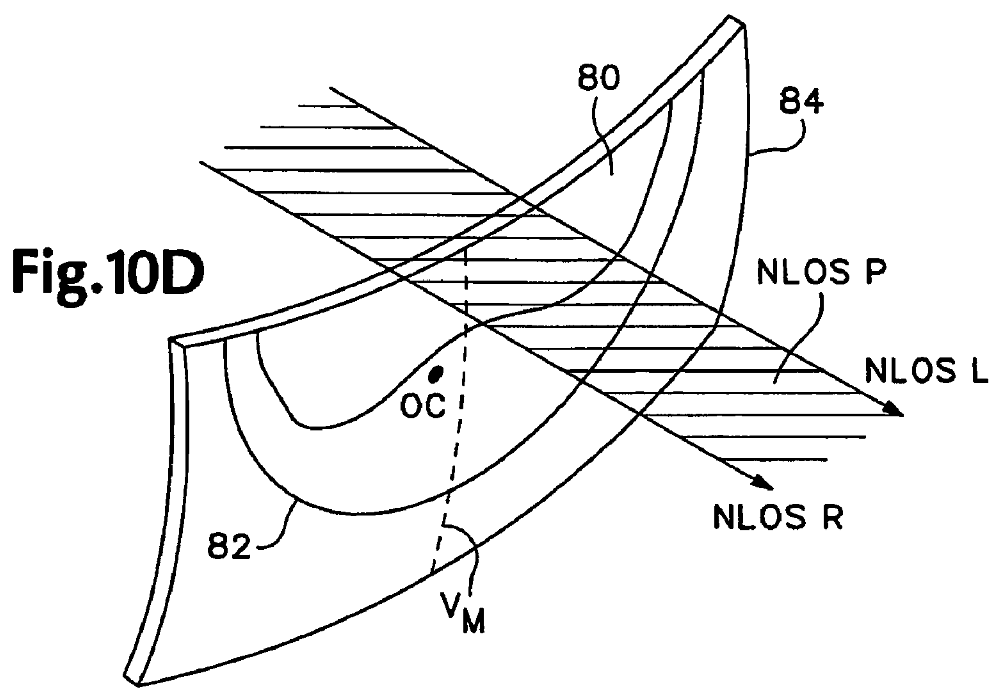
FIG. 10D is a perspective cutaway view of the curved surface of FIG. 1C taken along line 10C-10C.

FIG. 10D is a cutaway view of FIG. 10C along line 10D-10D (which extends through the NLOS of each eye). The normal line of sight plane NLOS P that contains the NLOS R of the right eye and NLOS L of the left eye is illustrated schematically in the figure.

In particular embodiments, the shield is cut from a decentered lens blank (such as lens blank 82) having an optical center OC that is spaced from the geometric center GC of the lens blank in at least a horizontal direction from vertical meridian VM or a vertical direction from horizontal plane HP, or both. In this manner, the shield has an optical axis that extends at a non-zero angle to the normal line of sight of the right and left eye in at least a horizontal or a vertical plane, or in both the horizontal and vertical planes. The optical axis is maintained substantially equidistant between the activity specific lines of sight of each the right and left eyes, such that the optical axis is not parallel to the normal lines of sight in at least one of a horizontal or vertical plane, or in both the horizontal and vertical planes.

Diminishing Peripheral Distortion

It has been found that peripheral distortion near the edge of a face shield lens while looking through the lens, as well as image shift that occurs when the line of sight passes across the edge of the lens, can be induced by distorted peripheral optical surfaces in a molded-to-shape lens. For example, one problem with injection molded lenses or lens blanks is that there are often injection molding artifacts peripherally in the lens, for example at the injection gate where plastic is injected into the lens cavity prior to hardening or with plastic flow turbulence near the edges of the lens cavity. Such peripheral distortion can be reduced by cutting away at least some of the edges of the shield. Optical material from all the edges of the entire shield, just one or more edges, or even portions of one or more edges, can be eliminated to improve the optical performance of the shield. In some embodiments of the shield that are designed for an ASLS that passes over a single interface edge of the shield (such as the lower or upper edge) as the vision shifts from the NLOS, only the peripheral plastic along that edge of the shield is cut away from the final shield.

Figure 11:
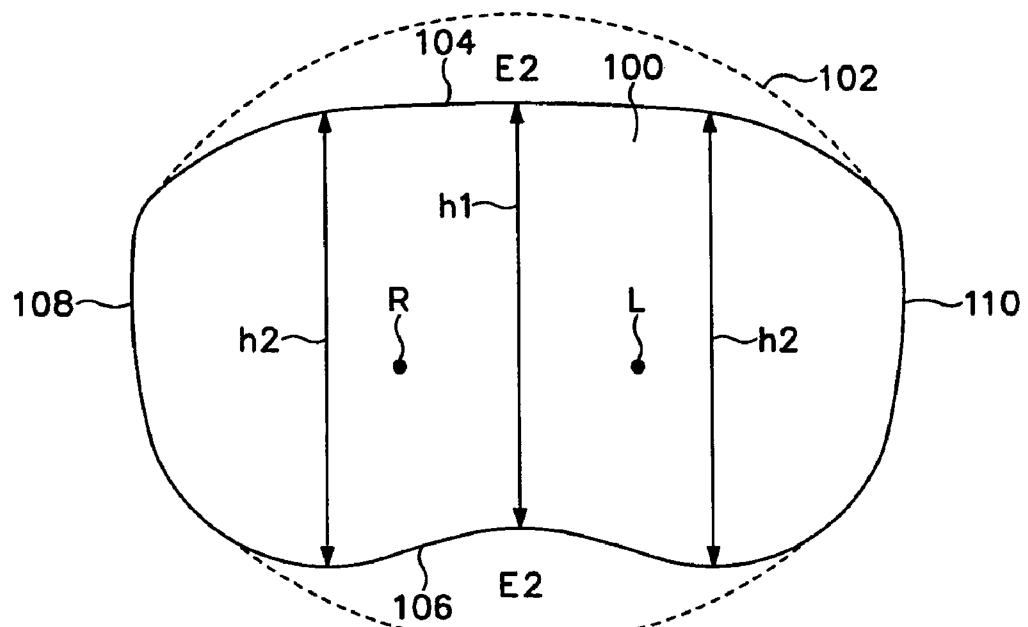
FIG. 11 is a schematic front view of a shield, illustrating a method for cutting away peripheral plastic material from some of the edges of the shield to improve the peripheral optical performance of the shield. The edges of the shield that are cut away are shown in phantom.

One example of a method of making a face shield 100 is shown in FIG. 11, wherein the face shield 100 is for example made in accordance with the design already described in connection with FIGS. 1-9. However, the shield 100 can also be a conventional face shield that does not have the optical design described herein for reducing optical distortion and/or shift at the periphery of the shield. Shield 100 can be obtained from an injection molded lens blank 102 that is slightly larger than shield 100, for example having excess plastic E 1 at the top edge 104 and E2 at the bottom edge 106, but not at side edges 108, 110. The excess plastic E1, E2 or both E1 and E2 can be cut from the shield to provide shield 100 with its finished shape shown in FIG. 11, in which the shield is cut to be mounted in an orientation that holds it in a desired relationship to the normal lines of sight R and L of the right and left eyes (where points R and L indicate the points at which each normal line of sight intersects shield 100), or in a desired relationship to the activity specific lines of sight ASLS. The finished shape has a reduced height center portion having a height $h_1$ that is less than the maximum height $h_2$ of the right and left eye portions of shield 100. Lens blank 102 (and resulting shield 100) can be injection molded to any desired shape, for example to produce a spherical or toroidal lens.

Figure 12:
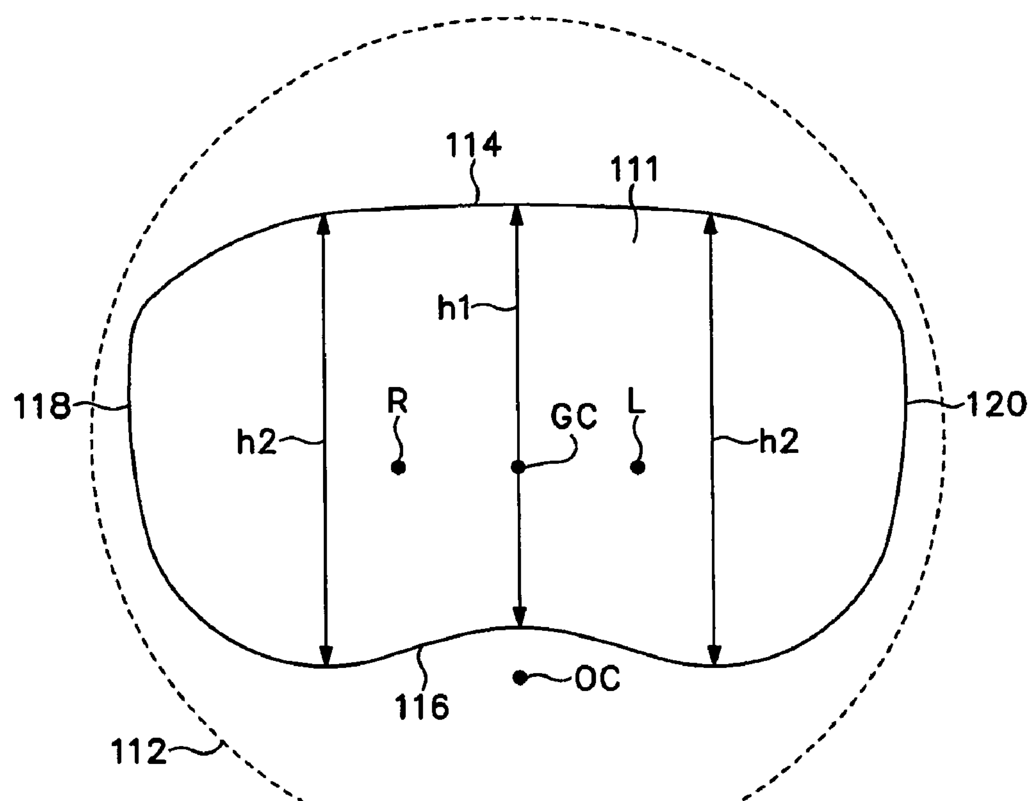
FIG. 12 is a view similar to FIG. 10, but showing the shield cut from a larger lens blank (illustrated in phantom) that helps reduce peripheral optical distortion of the resulting shield.

An alternative example of the method of manufacturing a face shield 111 is shown in FIG. 12, in which the face shield 111 is cut from a circular outline lens blank 112 that has been molded to the desired optical shape (such as a lens blank for a spherical or toroidal lens) having a decentered optical center OC. Face shield 111, once cut from lens blank 112, has upper edge 114, lower edge 116, right edge 118 and left edge 120. The optical center OC of the lens blank is "decentered" in that optical center OC is located at a different position on the lens blank than geometric center GC. In the disclosed example, the OC is located on the lens blank below the location from which lower edge 116 of shield 111 is to be cut, as in the design described in association with FIGS. 6A-6C. Hence cutting shield 111 from this location produces a face protector in which the OC is positioned in the desired location, in the plane of a vertical bisector through GC and OC that divides lens 111 into symmetric halves.

In the embodiment of FIG. 12, lens blank 112 has sufficient dimensions that shield lens 111 can be cut from entirely within the circular outline of lens blank 112, at a location that is interior to the edges of lens blank 112. Hence none of the edges of shield 111 coincide with the edges of lens blank 112, which eliminates from shield 111 the peripheral optical distortions that are often found in a lens blank. In the illustrated embodiment of FIG. 11, top and bottom edges 114, 116 are cut further from the edges of lens blank 112 than side edges 118, 120 which provides ever greater optical performance (and less molding induced distortion) for the upper and lower edges than for the side edges. Cutting shield 111 in this manner optimizes optical performance at the top and bottom edges of shield 111, and would be preferred for a shield that is designed for an ASLS that is above or below shield 111, or in which the ASLS crosses the top or bottom edge when moving from the NLOS.

As in FIG. 12, center height $h_1$ of shield 111 is less than the maximum height $h_2$ of shield 111 in the right and left eye portions. Shield 111 is also cut from lens blank 112 at a position that is selected relative to the NLOS of the right eye R and the left eye L.

In view of the many possible embodiments to which the principles of the invention may be applied, it should be recognized that the illustrated embodiment is only a preferred example of the invention and should not be taken as a limitation on the scope of the invention. Rather, the scope of the invention is defined by the following claims. We therefore claim as our invention all that comes within the scope and spirit of these claims.

The invention claimed is:

1. A protective shield for mounting in front of a face of a wearer in an as worn orientation, with the shield extending across the eyes and nose of the wearer for use in a specific activity involving a predetermined activity specific line of sight different than a straight ahead normal line of sight, the protective shield comprising:

an arcuate lens that, in the as worn orientation, to fully cover the eyes and nose of the wearer, the lens having an optical center and an apex, either or both of which can be on or off the lens, and a lower edge, and further, wherein a front center of curvature and a rear center of curvature, and an optical axis of the lens extends through the front center of curvature of the lens, the rear center of curvature of the lens, and the optical center of the lens; and wherein the optical center of the lens is displaced from the apex toward the predetermined activity specific line of sight other than the normal straight ahead line of sight, to a position that reduces object shift as the wearer shifts gaze from the normal straight ahead line of sight to the activity specific line of sight, wherein the optical axis of the lens is angled horizontally to a median plane by an angle of equal magnitude to a horizontal component of an angle of deviation of the predetermined activity line of sight from the normal straight ahead line of sight.

2. The protective shield of claim 1, wherein the predetermined activity specific line of sight is a sport specific line of sight.

3. The protective shield of claim 2, wherein the sport specific line of sight is a line of sight specific for ice hockey, football, baseball, skating, trail running, volleyball or automobile driving.

4. The protective shield of claim 1, wherein the optical axis is spaced from and substantially parallel to the predetermined activity specific line of sight.

5. The protective shield of claim 4, wherein the activity specific line of sight is below the lower edge of the lens and the optical center is at or below the lower edge of the lens.

6. The protective shield of claim 1, wherein the optical center is below the apex of the lens.

7. The protective shield of claim 1, wherein an optical axis extends through the optical center at an angle of at least 15 degrees from the normal straight ahead line of sight.

8. The protective shield of claim 7, wherein the activity specific line of sight is displaced either horizontally or vertically but not both horizontally and vertically from the normal straight ahead line of sight.

9. The protective shield of claim 8, wherein the optical axis of the lens is at an angle of at least 15 degrees below the normal line of sight.

10. The protective shield of claim 1, wherein the lens, in the as worn orientation, is mounted with reverse pantoscopic tilt.

11. The protective shield of claim 1, wherein the lens comprises a one-piece lens which is mounted with the normal line of sight extending through the lens and the optical axis of the lens extending through the optical center of the lens.

12. The protective shield of claim 1, further comprising a protective helmet to which the shield is mounted.

13. The protective shield of claim 12, wherein the protective helmet is a sports helmet.

14. The protective shield of claim 13, wherein the sports helmet is a hockey helmet.

15. The protective shield of claim 1, wherein the shield in the as worn orientation has an apex at a forwardmost location of the shield, or a virtual extension of the shield, and the optical center is displaced from the apex in a same direction that the activity specific line of sight is displaced away from the normal line of sight.

16. The protective shield of claim 15, wherein the optical center is displaced by at least 10 mm from the apex.

17. The protective shield of claim 15, wherein the optical center is displaced below the apex.

18. The protective shield of claim 1, wherein the optical axis of the lens that extends through the optical center is substantially parallel to and horizontally displaced from the activity specific line of sight (ASLS) of a right eye and a left eye, but not vertically displaced from the ASLS of the right eye and the left eye.

19. The protective shield of claim 1, wherein the optical axis of the lens is vertically spaced from and substantially parallel to a plane that extends through the activity specific line of sight of the fight eye and the activity specific line of sight of the left eye.

20. The protective shield of claim 19, wherein the optical axis has a horizontal component that is closer to the ASLS of either the right eye or the left eye, and a vertical component that is closer to the ASLS than the apex line is to the NLOS.

21. A protective shield for mounting in front of a face of a wearer in an as worn orientation, with the shield extending across a nose and right and left eyes of the wearer for use in a specific activity involving parallel predetermined activity specific lines of sight of the right eye and the left eye that are different than the straight ahead normal lines of sight of the right eye and the left eye, wherein the normal straight ahead lines of sight of the right and left eye extend through the shield in a normal line of sight plane, and the predetermined activity specific lines of sight extend in an activity specific line of sight plane, the protective shield comprising:

an arcuate lens that, in the as worn orientation, curves fully across the eyes and nose of the wearer, the lens having an apex that forms a forwardmost point of the lens in the as worn orientation, the lens further comprising an optical center through which extends an optical axis of the lens, wherein the optical center is not at the apex of the lens, and the optical axis is substantially parallel to the predetermined activity specific lines of sight of both the right eye and the left eye and spaced from the predetermined activity specific line of sight of at least one of the right eye and the left eye, and wherein the optical center is in a median plane, equidistant between the normal line of sight and each of the right and left eyes.

22. The protective shield of claim 21, wherein the optical axis of the lens is spaced closer to or father away from the predetermined activity specific line of sight than the optical axis is from an apex line that extends through the apex parallel to the normal line of sight.

23. The protective shield of claim 22, wherein a distance between the optical axis of the lens and the predetermined activity specific line of sight is less than a distance between the normal line of sight and the apex line.

24. The protective shield of claim 22, wherein a distance between the optical axis of the lens and the predetermined activity specific line of sight is greater than a distance between the normal straight ahead lines of and the apex line.

25. A protective shield for mounting in front of a face of a wearer in an as worn orientation, with the shield extending across a nose and right and left eyes of the wearer for use in a specific activity involving parallel activity specific lines of sight of the right eye and the left eye that are different than the straight ahead normal lines of sight of the right eye and the left eye, wherein the normal straight ahead lines of sight of the right and left eye extend through the shield in a normal line of sight plane, and the activity specific lines of sight extend in an activity specific line of sight plane, the protective shield comprising:

an arcuate lens that, in the as worn orientation, curves across the eyes and nose of the wearer, the lens having an apex that forms a forwardmost point of the lens in the as worn orientation, the lens further comprising an optical center through which extends an optical axis of the lens, wherein the optical center is in a median plane and is vertically downward from the apex of the lens, and the optical axis is substantially parallel to the activity specific lines of sight of both the right eye and the left eye and spaced from the activity specific line of sight of at least one of the right eye and the left eye, wherein the optical axis is laterally spaced from the activity specific line of sight of both the right eye and the left eye, but is closer to the activity specific line of sight of either the right eye or the left eye.

26. A shield for mounting on a protective helmet in an as worn orientation, the shield comprising:

a one piece arcuate lens that extends to fully cover and protect at least eyes and nose of a wearer when the lens is mounted to the protective helmet in the as worn orientation, such that a normal straight ahead line of sight extends through the lens when the lens is mounted in the as worn orientation and an apex of the lens is located at a forwardmost point of the lens or on a virtual extension of the lens; and wherein the lens has at least a front center of curvature and a rear center of curvature, and an optical axis of the lens extends through the front center of curvature, the rear center of curvature and an optical axis, and the optical axis of the lens extends through the optical center of the lens below the apex, wherein the optical center is in a median plane, equidistant between the activity line of sight of the right eye and the left eye.

27. The shield of claim 26, wherein the lens comprises an upper edge and a lower edge, and the optical axis of the lens extends through the optical center at or below the lower edge of the lens, at an angle of at least 5 degrees to the normal line of sight.

28. The shield of claim 27, wherein the optical center is at least about 5 rom below the lower edge of the lens.

29. The shield of claim 27, wherein the optical center is at least about 10 rom below the lower edge of the lens.

30. The shield of claim 29, wherein the lens is substantially zero power.

31. The protective shield of claim 1, wherein the activity specific line of sight does not extend through the shield.

* * * * *